US010426867B2

(12) United States Patent
Runge et al.

(10) Patent No.: US 10,426,867 B2
(45) Date of Patent: Oct. 1, 2019

(54) BIOCOMPATIBLE POLYCAPROLACTONE FUMARATE FORMULATIONS

(75) Inventors: Michael Brett Runge, Pine Island, MN (US); Michael J. Yaszemski, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/009,987

(22) PCT Filed: Apr. 4, 2012

(86) PCT No.: PCT/US2012/032131
§ 371 (c)(1),
(2), (4) Date: Dec. 17, 2013

(87) PCT Pub. No.: WO2012/138732
PCT Pub. Date: Oct. 11, 2012

(65) Prior Publication Data
US 2014/0099278 A1    Apr. 10, 2014

Related U.S. Application Data

(60) Provisional application No. 61/473,347, filed on Apr. 8, 2011.

(51) Int. Cl.
*A61L 27/18* (2006.01)
*A61L 27/26* (2006.01)
*C08G 63/08* (2006.01)
*C08G 63/60* (2006.01)

(52) U.S. Cl.
CPC ............. *A61L 27/18* (2013.01); *A61L 27/26* (2013.01); *C08G 63/08* (2013.01); *C08G 63/60* (2013.01)

(58) Field of Classification Search
CPC .......... C08L 67/04; C08G 63/08; C08G 63/60
See application file for complete search history.

(56) References Cited

U.S. PATENT DOCUMENTS

| 3,169,945 A * | 2/1965 | Young et al. .................. 528/355 |
| 2007/0043202 A1 * | 2/2007 | Yaszemski et al. .......... 528/310 |
| 2008/0004368 A1 | 1/2008 | Wang et al. |

FOREIGN PATENT DOCUMENTS

| GB | 1394396 | 5/1975 |
| JP | 2008519892 | 6/2006 |
| JP | 2007528909 | 10/2007 |
| WO | 2006053031 A2 | 5/2006 |
| WO | 2012138732 A1 | 10/2012 |

OTHER PUBLICATIONS

Chung, et al., Syntheses and Evaluation of Biodegradable Multifunctional Polymer Networks, European Polymer Journal, 2003, 39:1817-1822.
Kweon, et al., A Novel Degradable Polycaprolactone Networks for Tissue Engineering, Biomaterials, 2003, 24:801-808.
Temenoff, et al., Effect of Poly(ethylene glycol) Molecular Weight on Tensile and Swelling Properties of Oligo(poly(ethylene glycol)fumarate) Hydrogels for Cartilage Tissue Engineering, J. Biomed. Mater. Res., 2002, 59:429-437.
Wang, et al., Photo-Crosslinked Poly(E-caprolactone fumarate) Networks: Roles of Crystallinity and Crosslinking Density in Determining Mechanical Properties, Polymer, 2008, 49:5692-5699.
Wiggins, Design of Bioabsorbable, Amorphous Polymer Networks and Composites, Publication Date of Jan. 1, 1992, Retrieved from Energy Citations Database, www.osti.gov/energycitations/product.biblio.jsp?osti_id=7153129, on Mar. 23, 2007.
Xie, et al., Experimental Investigation on the Reliability of Routine Sec-Malls for the Determination of Absolute Molecular Weights in the Oligomeric Range, Polymer, 2002, 43:3973-3977.
International Search Report dated Jul. 27, 2012 for International Application No. PCT/US2012/032131.
Runge et al., "Reformulating polycaprolactone fumarate to eliminate toxic diethylene glycol: Effects of polymeric branching and autoclave sterilization on material properties"; Sep. 1, 2011; Acta Biomatarials, vol. 8, pp. 133-143.
Choi, et al., Synthesis and Characterization of a Series of Star-Branched Poly (Epsilon-Caprolactone)s with the Variation in Arm Numbers and Lengths, Polymer, 2005, 46:9725-9735.
Lang, et al., Synthesis and Structural Analysis of Functionalized Poly (Epsilon-Caprolactone)-Based Three-Arm Star Polymers, J. Polym. Sci. Part A: Polym. Chem., 2002, 40:1127-1141.
European Patent Office, Supplementary European Search Report, Application No. 12768537.8, dated Apr. 16, 2015.
Office Action in Japanese Patent Application 2014-503943.

* cited by examiner

*Primary Examiner* — Anna R Falkowitz
(74) *Attorney, Agent, or Firm* — Quarles & Brady LLP

(57) ABSTRACT

A polycaprolactone fumarate polymer useful as a matrix material for a biocompatible scaffold for tissue engineering applications is disclosed. The polycaprolactone fumarate polymer can be prepared by reacting caprolactone with an alkane polyol to prepare a polycaprolactone precursor, and then reacting the polycaprolactone precursor with fumaric acid or a salt thereof to prepare the polycaprolactone fumarate polymer. The use of an alkane diol, such as 1,2-propanediol, provides a linear polycaprolactone diol precursor. The use of an alkane triol, such as glycerol, provides a branched polycaprolactone triol precursor. The biocompatible polycaprolactone fumarate formulation releases no diethylene glycol or other undesirable byproducts during degradation.

10 Claims, 22 Drawing Sheets

POLYCAPROLACTONE FUMARATE

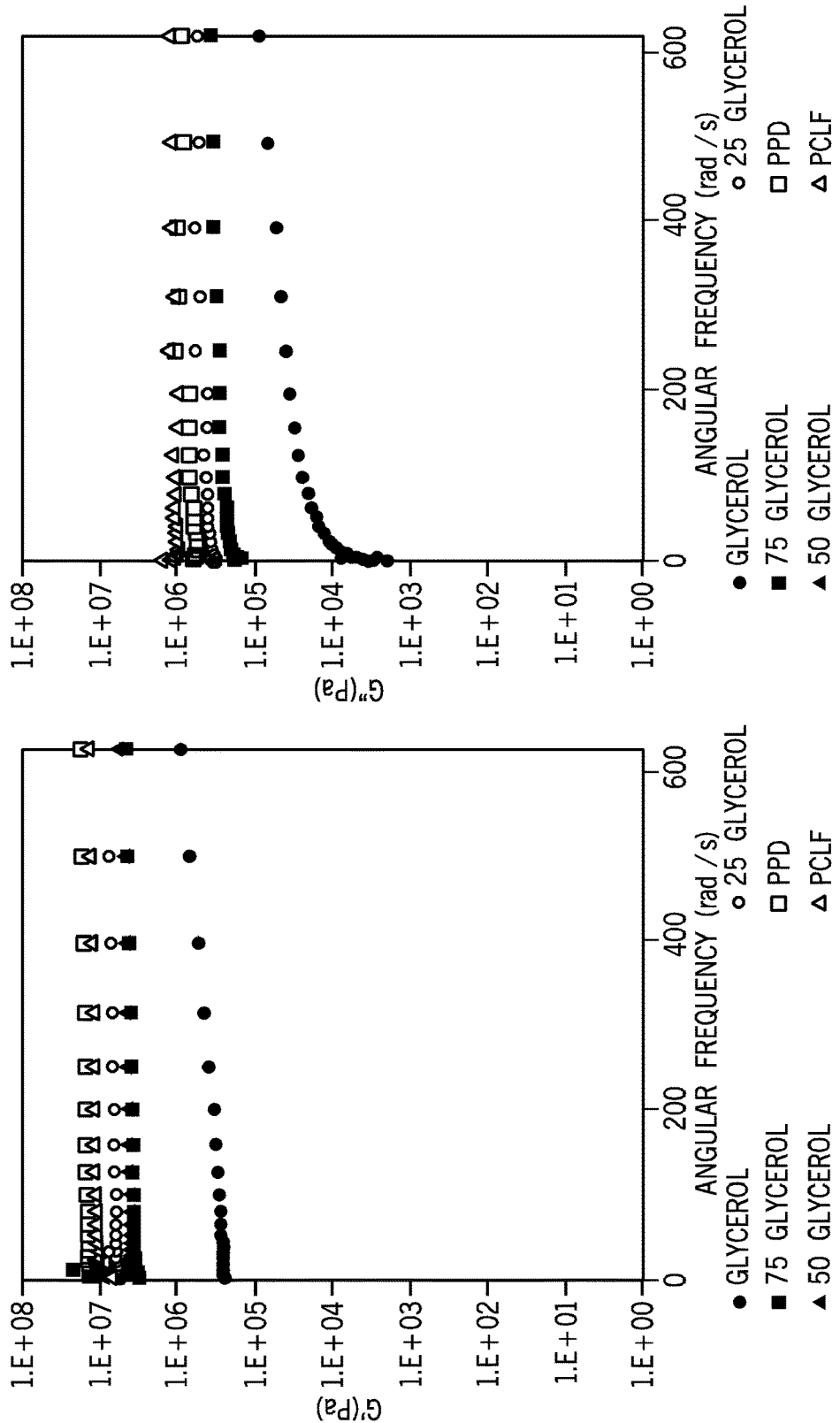

BIOCOMPATIBLE POLYCAPROLACTONE FUMARATE FORMULATIONS

CROSS-REFERENCES TO RELATED APPLICATIONS

This application is a 371 application of PCT/US2012/032131 filed Apr. 4, 2012 which claims the benefit of U.S. provisional application 61/473,347 filed Apr. 8, 2011, which is incorporated herein by reference in its entirety.

STATEMENT REGARDING FEDERALLY SPONSORED RESEARCH

This invention was made with government support under NIH/NIAMS AR056950 and (MRMC) W81XWH-08-2-0034 awarded by National Institutes of Health. The government has certain rights in the invention.

BACKGROUND OF THE INVENTION

1. Field of the Invention

This invention relates to the synthesis of a polycaprolactone fumarate polymer useful as a material for a biocompatible scaffold for tissue engineering.

2. Description of the Related Art

Polycaprolactone fumarate (PCLF) is a cross-linkable derivative of polycaprolactone (PCL) that has been shown to be promising material for tissue engineering applications involving both the repair of segmental nerve defects as well as a bone substitute. PCLF has previously been synthesized by condensation polymerization of fumaryl chloride with a polycaprolactone ether diol of molecular weights 530, 1200, or 2000 g mol$^{-1}$. Previous work has shown that PCLF synthesized from PCL ether diol with an $M_n$ of 2000 g mol$^{-1}$ results in PCLF with an $M_n$ of 7,000 to 18,000 g mol$^{-1}$, and has the most favorable material properties over other PCLF formulations synthesized from PCL 530 or 1250. Therefore PCLF synthesized from PCL$_{2000}$ has been used for the production of nerve conduits to repair segmental nerve defects. These PCLF nerve conduits have been shown to support robust nerve regeneration across the one centimeter rat sciatic nerve defect model and have warranted future clinical studies.

In preparation for upcoming clinical trials, the potential degradation products released from polycaprolactone fumarate scaffolds were analyzed. During the course of this degradation study, it was determined that diethylene glycol (also known as 2-hydroxyethyl ether) (DEG) can be released during hydrolysis as one degradation product from the previously studied polycaprolactone fumarate. The release of diethylene glycol is of concern because it is has been reported to be a toxin and makes up roughly 5 percent of a polycaprolactone fumarate composition formed from polycaprolactone ether diol, an amount that currently exceeds United States Food and Drug Administration limits.

What is needed therefore is a biocompatible polycaprolactone fumarate formulation that releases no diethylene glycol or other undesirable byproducts during degradation.

SUMMARY OF THE INVENTION

It was determined that the source of diethylene glycol in polycaprolactone fumarate scaffold degradation was the polycaprolactone ether diol used to prepare polycaprolactone fumarate. In order to circumvent the release of this degradation product, new polycaprolactone fumarate compositions were synthesized using linear polycaprolactone diols or branched polycaprolactone triols. One example polycaprolactone diol was synthesized from 1,2 propanediol (PPD). One example polycaprolactone triol was synthesized from glycerol (GLY). These biocompatible alcohols can be used as initiators for the polymerization of polycaprolactone.

Although both 1,2 propanediol and glycerol can be used to produce polycaprolactone and the subsequent polycaprolactone fumarate, the resulting polymeric architectures are different. The 1,2 propanediol results in linear polycaprolactone diol that is used as a precursor to the synthesis of polycaprolactone fumarate, while glycerol results in a tri-branched polycaprolactone structure producing a branched polycaprolactone fumarate architecture. The differences in the polymeric architecture in turn effects the thermal, crystalline, and mechanical properties.

We have shown that polycaprolactone fumarate produced from polycaprolactone initiated from 1,2 propane diol exhibits material properties similar to the previously studied polycaprolactone fumarate, and have shown that the material properties are dramatically altered by effectively changing the polymeric architecture. Thus, the invention provides for the synthesis and characterization of new polycaprolactone fumarate compositions. We have characterized the thermal, crystalline, rheological, and mechanical properties of the new polycaprolactone fumarate compositions and combinations thereof and have determined the effect of autoclave sterilization on these material properties.

These and other features, aspects, and advantages of the present invention will become better understood upon consideration of the following detailed description, drawings, and appended claims.

BRIEF DESCRIPTION OF THE DRAWINGS

FIG. 9C shows rheological measurements for storage modulus for different PCLF compositions.

FIG. 9D shows rheological measurements for loss modulus for different PCLF compositions.

FIGS. 11, 11A, 11B, 11C, 11D, 11E, and 11F show PC12 cell attachment and morphology. MTS assay showing the number of cells attached after 24 hours. Fluorescence microscopy showing PC12 cell morphology after 24 hours for: FIG. 11A—$PCLF_{PPD100}$; FIG. 11B—$PCLF_{PPD75}PCLF_{GLY25}$; FIG. 11C—$PCLF_{PPD50}PCLF_{GLY50}$; FIG. 11D—$PCLF_{PPD25}PCLF_{GLY75}$; FIG. 11E—$PCLF_{GLY100}$; and FIG. 11F—$PCLF_{DEG}$.

DETAILED DESCRIPTION OF THE INVENTION

As used herein, a "biocompatible" material is one which stimulates only a mild, often transient, implantation response, as opposed to a severe or escalating response. As used herein, a "biodegradable" material is one which decomposes under normal in vivo physiological conditions into components which can be metabolized or excreted. As used herein, a "bioresorbable" material is one that breaks down over a finite period of time due to the chemical/biological action of the body. By "injectable", we mean the copolymer may be delivered to a site by way of a medical syringe. By "self-crosslinkable", we mean the functional groups of a polymer according to the invention may crosslink with the functional groups of the same polymer or another polymer according to the invention without a cross-linking agent that forms crosslinks between the functional groups of a polymer according to the invention and the functional groups of the same or another polymer according to the invention.

The term "number average molecular weight" ($M_n$) refers to the total weight of all the molecules in a polymer sample divided by the total number of moles present ($M_n=\Sigma_i N_i M_i / \Sigma_i N_i$). Although number average molecular weight can be determined in a variety of ways, with some differences in result depending upon the method employed, it is convenient to employ gel permeation chromatography or end-group analysis. As used herein, "weight average molecular weight" is defined as $M_w=\Sigma_i N_i M_i^2 / \Sigma_i N_i M_i$. Although weight average molecular weight ($M_w$) can be determined in a variety of ways, with some differences in result depending upon the method employed, it is convenient to employ gel permeation chromatography. As used herein, the term "polydispersity" or "polydispersity index" (PDI) refers to the ratio of a materials' "weight average molecular weight" divided by its "number average molecular weight" ($M_w/M_n$).

In one non-limiting example embodiment, the invention is a polymer having the Formula (I):

$$H-A_1-B-A_2-C-A_1-B-A_2-H \qquad (I)$$

wherein $A_1$ is

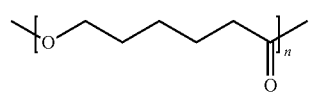

$A_2$ is

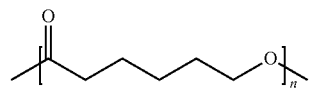

B is —O—X—O— wherein X is selected from the group consisting of ethylene, trimethylene, tetramethylene, pentamethylene, $C_1$-$C_5$ alkylethylene, $C_1$-$C_5$ alkyltrimethylene, $C_1$-$C_5$ alkyltetramethylene, and $C_1$-$C_5$ alkylpentamethylene; C is

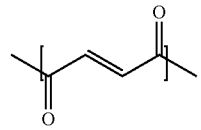

and geometric isomers thereof; and n is an integer from 1 to 50.

Figure 1A:
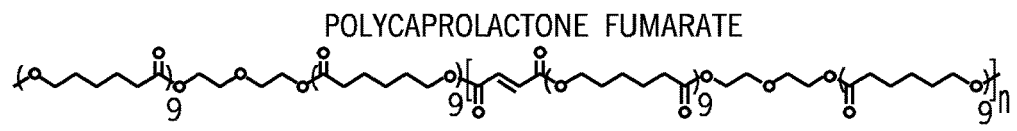
FIG. 1A shows the chemical structure of polycaprolactone fumarate prepared from a precursor synthesized using diethylene glycol.
Figure 1B:
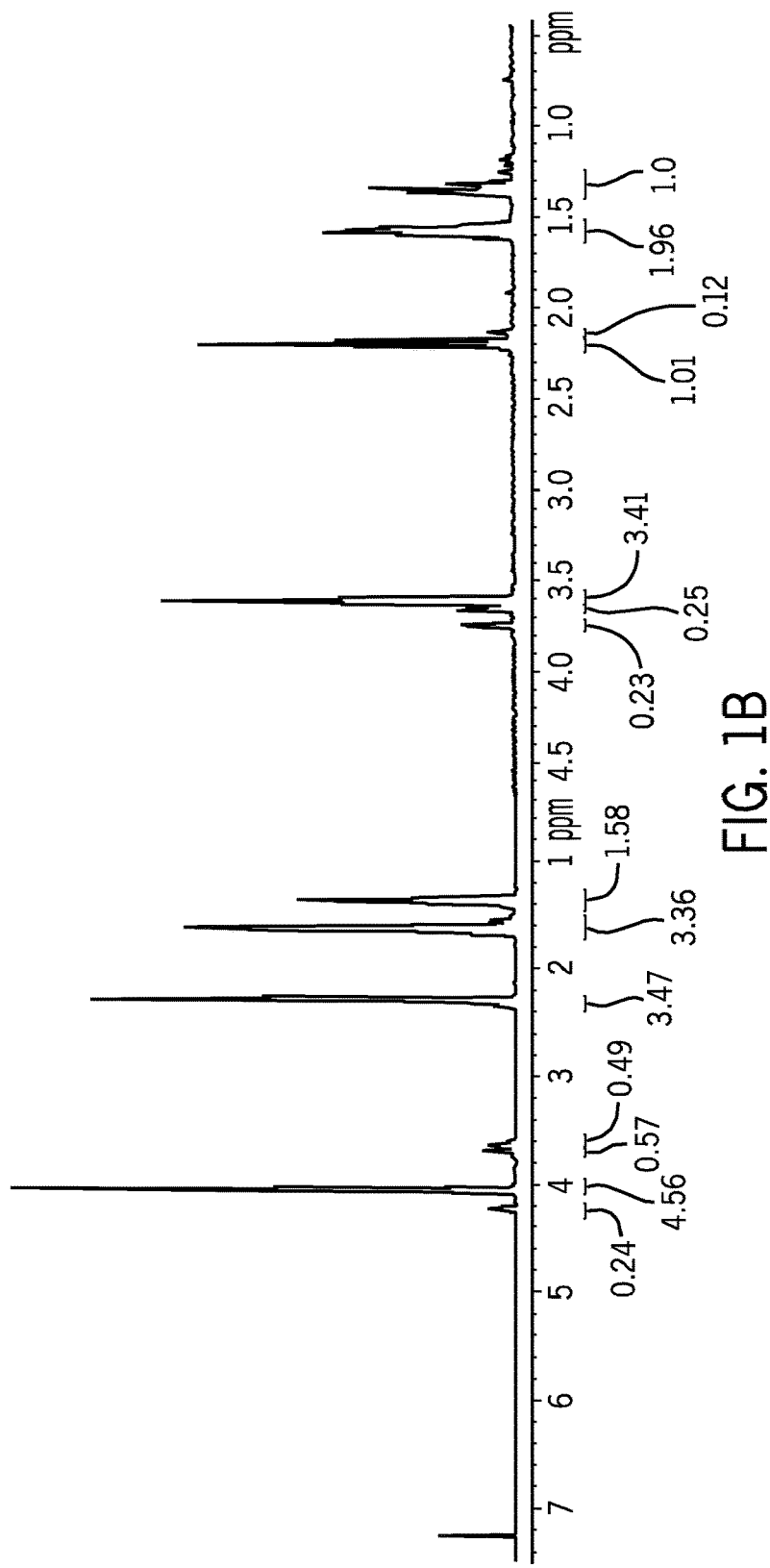
FIG. 1B shows an H NMR of polycaprolactone (PCL$_{DEG}$) and polycaprolactone fumarate (PCLF$_{DEG}$) degradation products wherein PCLF$_{DEG}$ is a polycaprolactone fumarate polymer such as FIG. 1A produced by reacting fumaryl chloride with a polycaprolactone precursor polymer synthesized from diethylene glycol (PCL$_{DEG}$).
Figure 2:
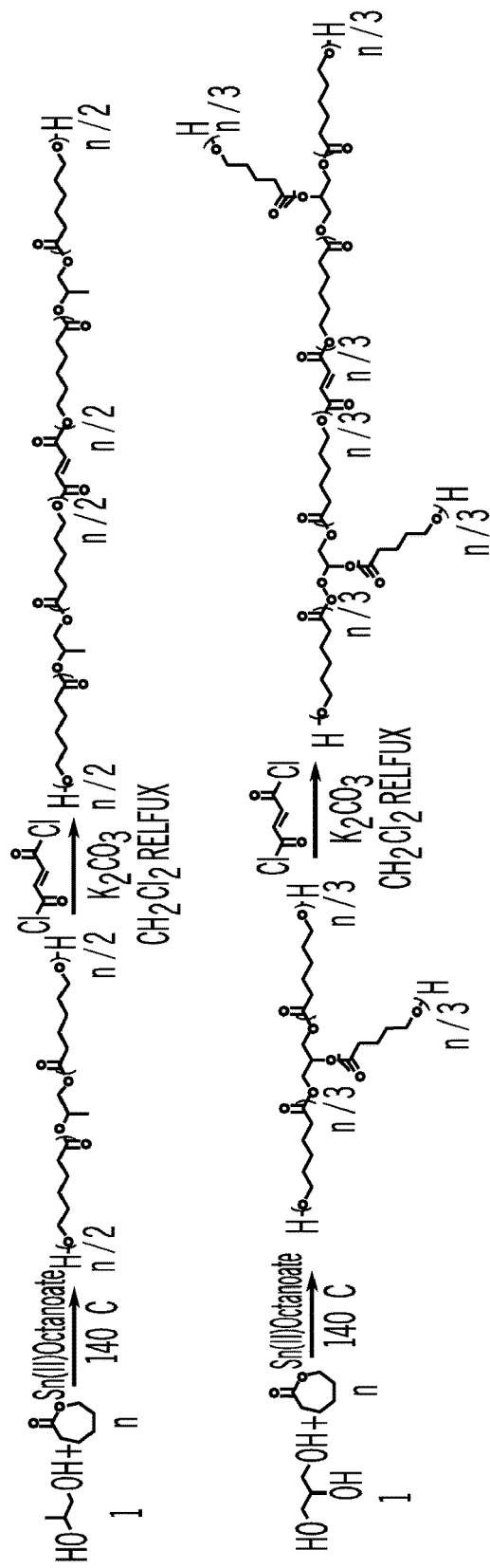
FIG. 2 shows a synthetic scheme of PCLF PPD and PCLF Glycerol wherein PCLF PPD is a polycaprolactone fumarate polymer produced by reacting fumaryl chloride with a polycaprolactone precursor polymer synthesized from 1,2 propane diol, and wherein PCLF Glycerol is a polycaprolactone fumarate polymer produced by reacting fumaryl chloride with polycaprolactone precursor polymers synthesized from glycerol.

FIG. 2 shows a method for synthesizing one example of this embodiment of the invention wherein caprolactone is reacted with an alkane polyol (e.g., 1,2-propanediol) to prepare a polycaprolactone precursor, and the polycaprolactone precursor is reacted with fumaric acid or a salt thereof. In a preferred embodiment, n is an integer from 1 to 20, more preferably from 1 to 10. In another preferred embodiment, X is methylethylene.

In some embodiments, the polymer has a number average molecular weight in the range of 5,000 to 15,000 g mol$^{-1}$ or the polymer has a polydispersity index in the range of 1 to 6.

In another non-limiting example embodiment, the invention is a crosslinkable, biodegradable material comprising the polymer having the Formula (I) as described above and a free radical initiator. In some embodiments the material does not include a crosslinking agent.

In another non-limiting example embodiment, the invention is a scaffold comprising a biodegradable matrix comprising the polymer having the Formula (I) as described above. In some embodiments, diethylene glycol is not released during hydrolysis of the scaffold. In other embodiments, the scaffold maintains its geometrical structure and dimensions throughout an autoclave sterilization process or the scaffold maintains mechanical properties within an order of magnitude during an autoclave sterilization process.

In another non-limiting example embodiment, the invention is a polymer having the Formula (II):

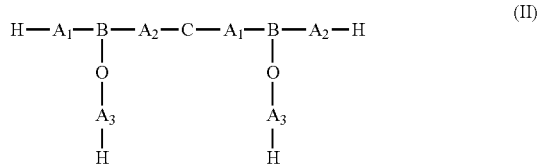

wherein $A_1$ is

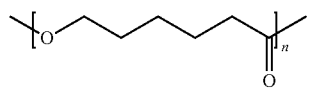

$A_2$ is

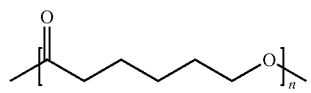

$A_3$ is

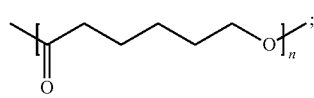

B is —O—X—O— wherein X is selected from the group consisting of propanetriyl, butanetriyl, pentanetriyl, $C_1$-$C_5$ alkyl propanetriyl, $C_1$-$C_5$ alkyl butanetriyl, and $C_1$-$C_5$ alkyl pentanetriyl; C is

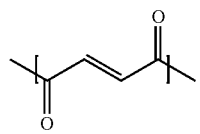

and geometric isomers thereof; and n is an integer from 1 to 50.

FIG. 2 shows a method for synthesizing one example of this embodiment of the invention wherein caprolactone is reacted with an alkane polyol (e.g., glycerol) to prepare a polycaprolactone precursor, and the polycaprolactone precursor is reacted with fumaric acid or a salt thereof. In a preferred embodiment, n is an integer from 1 to 20, more preferably from 1 to 10. In another preferred embodiment, X is propanetriyl.

In some embodiments, the polymer has a number average molecular weight in the range of 5,000 to 15,000 g mol$^{-1}$ or the polymer has a polydispersity index in the range of 1 to 6.

In another non-limiting example embodiment, the invention is a crosslinkable, biodegradable material comprising the polymer having the Formula (II) as described above and a free radical initiator. In some embodiments the material does not include a crosslinking agent.

In another non-limiting example embodiment, the invention is a scaffold comprising a biodegradable matrix comprising the polymer having the Formula (II) as described above. In some embodiments, diethylene glycol is not released during hydrolysis of the scaffold. In other embodiments, the scaffold maintains its geometrical structure and dimensions throughout an autoclave sterilization process or the scaffold maintains mechanical properties within an order of magnitude during an autoclave sterilization process.

In another non-limiting example embodiment, the invention is a scaffold for tissue regeneration. The scaffold includes a blend of the polymer of Formula (I) described above and the polymer of Formula (II) described above. In a preferred embodiment, the scaffold includes 20 wt. % to 80 wt. % of the polymer of Formula (I) and 20 wt. % to 80 wt. % of the polymer of Formula (II). In a more preferred embodiment, the scaffold includes 40 wt. % to 60 wt. % of the polymer of Formula (I) and 40 wt. % to 60 wt. % of the polymer of Formula (II).

In some embodiments, the polymer of Formula (I) is methylethylene, the polymer of Formula (II) is propanetriyl, or the polymer of Formulas (I) or (II) have a number average molecular weight in the range of 5,000 to 15,000 g mol$^{-1}$ or a polydispersity index in the range of 1 to 6. In some embodiments, the scaffold maintains its geometrical structure and dimensions throughout an autoclave sterilization process or the scaffold maintains mechanical properties within an order of magnitude during an autoclave sterilization process.

In another non-limiting example embodiment, the invention is a polymer prepared by a process including reacting caprolactone with an alkane polyol to prepare a polycaprolactone precursor and reacting the polycaprolactone precursor with fumaric acid or a salt thereof. In one embodiment, the polycaprolactone precursor is reacted with fumaryl chloride.

The alkane polyols for use in synthesizing the polycaprolactone precursor are preferably alkane polyols having 2 to 5 carbon atoms. Preferably, the alkane polyol is a biocompatible $C_{2-5}$ polyol.

Non-limiting examples include: (i) alkane diols, such as 1,2-ethanediol, 1,2-propanediol, 1,3-propanediol, 1,2-butanediol, 1,3-butanediol, 1,4-butanediol, 2,3-butanediol and 1,5-pentanediol; and (ii) alkanetriols such as glycerol (1,2, 3-propanetriol). Suitable molar ratios of caprolactone to the alkane polyol are 1:1 to 50:1, more preferably 10:1 to 30:1, and more preferably 15:1 to 25:1. Preferably, the alkane polyol is a biocompatible $C_{2-5}$ polyol.

In some embodiments the polycaprocatone precursor has a number average molecular weight in the range of 1,000 to 5,000 g mol$^{-1}$, preferably in the range of 1,000 to 3,000 g mol$^{-1}$ or in the range of 1,500 to 2,500 g mol$^{-1}$. The polymer may be prepared by a process involving two separate reactions, wherein the polycaprolactone precursor is isolated, or the polycaprolacone precursor and the polymer may be prepared in one reaction vessel without isolation of the polycaprolactone precursor.

The polycaprolactone fumarate which is the subject of this invention can be provided as a resorbable and semi-crystalline polymer with a melting point between 50-70 degrees centigrade depending on the molecular weight of the polycaprolactone fumarate. Above its melting point, the polycaprolactone fumarate can be a free flowing liquid which can be physically mixed with other formulation components such as porogen, initiator, crosslinking agent, accelerator, diluent, foaming agent, buffering agent, inhibitor catalyst, growth factors, particulate and fiber reinforcing materials, and stabilizers in free or encapsulated form and the polycaprolactone fumarate can be injected via a syringe to fabricate a scaffold used for regeneration of biological tissues. Below the melting point, for example at human biological temperature of 37° C. (98.6° F.), the polycaprolactone fumarate can become a solid and harden by physical as well as chemical crosslinking.

Physical crosslinking can take place by partial crystallization of polycaprolactone segments of the polycaprolactone fumarate chains. Chemical crosslinking can occur by cross-linking of double bonds of the fumarate groups of polycaprolactone fumarate chains in the presence of suitable initiator, accelerator, or crosslinking agent. However, the material can be self-crosslinkable such that a crosslinking agent is not needed. The extent of physical and chemical crosslinking can be controlled independently by the molecular weight of polycaprolactone, the molecular weight of the polycaprolactone fumarate macromer, and the ratio of fumarate to polycaprolactone in the polycaprolactone fumarate macromer. The degradation behavior of the polycaprolactone fumarate macromer can be also controlled by the molecular weight of polycaprolactone, the molecular weight of the polycaprolactone fumarate macromer, and the ratio of fumarate to polycaprolactone in the polycaprolactone fumarate macromer.

A biocompatible and bioresorbable polycaprolactone fumarate biomaterial according to the invention can have a melting point between 50-70° C. and a hardening point between 30-40° C. This unique property makes this biomaterial useful in fabrication of injectable and in-situ hardening scaffolds for application in skeletal reconstruction. Application of this invention can be as an injectable bioresorbable synthetic bone substitute or as an injectable bioresorbable bone cement with controlled degradation behavior. Alternatively, the polycaprolactone fumarate biomaterial can be injected into a mold for preparation of a scaffold that is thereafter implanted in the body.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Various features and advantages of the invention are set forth in the following claims.

EXAMPLES

The following Examples have been presented in order to further illustrate the invention and are not intended to limit the invention in any way.

I. Methods

A. Materials

All chemicals and reagents were purchased from Fisher or Aldrich in the highest available purity and used as is unless otherwise noted. Epsilon-caprolactone was distilled under vacuum at 100° C. and stored under a nitrogen atmosphere until use. Fumaryl chloride was distilled before use.

B. Synthesis of Polycaprolactones

Tin(II)ethylhexanoate (2.08 g, 0.005 mol) and 1,2 propane diol (9.8 g, 0.128 mol) were added to a Schlenk flask with a stir bar. The flask was pumped down and backfilled with $N_2$ three times followed by the addition of ε-capolactone under $N_2$. The reaction vessel was placed in a 140° C. oil bath for 1 hour and then cooled to room temperature. The polymer melt solidified upon cooling and was dissolved in methylene chloride followed by precipitation into petroleum ether. The precipitated polymer was dried under vacuum at 60° C. and used as is.

C. Synthesis of Polycaprolactone Fumarate

Potassium carbonate (18.0 g, 0.13 mol) was added to a three neck flask fitted with a reflux condenser and purged with $N_2$. Polycaprolactone diol (225 g, 0.11 mol) was dissolved in 600 mL of methylene chloride and added to the flask. Freshly distilled fumaryl chloride (17.2 g, 0.11 mol) dissolved in 20 mL methylene chloride was added dropwise to the reaction vessel and heated to reflux for 12 hours. The reaction was then filtered to remove $K_2CO_3$, and precipitated into petroleum ether. The polymer was dried and used as is.

D. One Pot Synthesis of Polycaprolactone and Polycaprolactone Fumarate

To previously dried Schlenk Flask, Tin(II)ethylhexanoate (0.406 g, 0.001 mol) was added followed by 1,2 propane diol (3.81 g, 0.05 mol). The Schlenk Flask was evacuated to 1 mmHg and backfilled with $N_2$ three times. Caprolactone (103 g, 0.9 mol) was added to the vessel, and the vessel was heated to 140° C. for 40 minutes, and then cooled to 60° C. At this point GPC analysis shows the polymerization of caprolactone was complete. 300 mL tetrahydrofuran was added to the Schlenk Flask and the reaction was further cooled to 23° C. $K_2CO_3$ was added to the Schlenk Flask followed by dropwise addition of fumaryl chloride (7.23 g, 0.0473 mol). The reaction mixture was stirred for 20 hours at 23° C. The solution was diluted with 400 mL tetrahydrofuran and the solution was decanted to separate from $K_2CO_3$ before adding 100 mL water. The solution was stirred for 1 hour, and then dried over $MgSO_4$. The majority of tetrahydrofuran was evaporated, and the polymer was dissolved in methylene chloride. The methylene chloride layer was dried with $MgSO_4$, filtered, and then evaporated. The polymer was precipitated into petroleum ether, dried, and used as is.

E. Polymer Characterization

Polymer molecular weights were measured using gel permeation chromatography (GPC). The GPC system consisted of a Waters 2410 refractive index detector, 515 HPLC pump, and 717 Plus autosampler, and a Styragel HR4E column. THF was used as the eluent at 1 mL/min. Polystyrene standards were used to determine the $M_n$ and PDI. $^1$H NMR spectra were recorded on a 300 MHz Varian NMR in $CDCl_3$.

F. Scaffold Fabrication

Polycaprolactone fumarate (PCLF) (3.0 g) was dissolved in 1 mL methylene chloride. Photo-initiator Irgacure 819 acyl-phosphine oxide (0.3 g) was dissolved in 3 mL methylene chloride, and 300 µL was added to the PCLF. The mixture was gently heated and vortexed to ensure a homogenous solution. The mixture was poured into glass molds for film and tube fabrication. The molds consisted of two glass plates separated by 0.5 mm. The molds and containing polymer mixes were placed in a UV chamber and irradiated at 315-380 nm for 1 hour to induce cross-linking.

G. PCLF Degradation

PCLF scaffolds were degraded in $D_2O$ containing 1 M NaOH at 37° C.

H. Autoclave Sterilization

Preformed films or tube scaffolds were packaged in sterilization pouches and autoclaved at 125° C. at 23 psi for 25 minutes.

I. Thermal Analysis

Thermogravimetric analysis (TGA) was performed on a TA Instruments Q500 thermal analyzer. Samples were heated from room temperature to 800° C. at a rate of 5° C. $min^{-1}$ under flowing nitrogen. Dynamic scanning calorimetry (DSC) was performed on a TA Instruments Q1000 differential scanning calorimeter. Under a nitrogen atmosphere, the sample underwent a heat-cool-heat cycle to ensure the same thermal history between samples. Samples were heated from room temperature to 100° C., then cooled to −80° C., and then heated to 150° C. at a rate of 5° C. $min^{-1}$.

J. Mechanical Testing

Mechanical Testing was performed on a TA Instrument Dynamic Mechanical Analyzer 2980. To analyze the three-point bending properties of the materials, cylindrical tube geometry scaffolds were mounted on a TA instruments DMA 2980 three-point bending clamp and a preload force of 0.02 N was applied. A ramping force of rate 1.0 N/min was applied until material failure or 18 N achieved. The samples flexural moduli were measured at room temperature, after equilibration at 37° C. overnight, and at room temperature after autoclave. The TA instruments' universal analysis software was used to identify the materials' flexural modulus at 5% strain for all materials. For stretching and tensile measurements, PCLF films were cut into a dog bone shape with a diameter of 2.1 mm. Half of the samples were kept in water at room temperature and half at 37° C. in a water bath after previously had been heated to 50° C. Each scaffold was mounted on a TA instruments Dynamic Mechanical Analyzer (DMA) 2980 tension clamp. The force applied on the sample started at 0.02 Newton (N) and increased at a rate of 1.0 N/min until reaching either 18.0 N or the material's failure point. Subsequently the tensile modulus of the scaffolds was determined by measuring the slope of the linear part of the stress/strain curve.

K. Rheometry

The linear viscoelastic properties of cross-linked PCLF polymer films were measured using a torsional dynamic mechanical analyzer (TA Instruments AR2000 rheometer). The linear viscoelastic region was determined using a strain sweep at a frequency of 1 Hz. A strain of 0.05% and oscillating stress 10 kPa were determined to be within the linear viscoelastic region for all polymers and were used for all further rheometry measurements. A frequency sweep from 0.1 to 628.3 rad/s was used to measure storage (G') and loss (G") moduli.

L. In Vitro Studies Using PC12 Cells

DMEM media supplemented with 10% heat inactivated horse serum, 5% heated inactivated fetal bovine serum, and 0.5% penicillin/streptomycin was used for PC12 cell culture. PCLF composite materials were fabricated into disks of diameters 1.0 cm as described above, sterilized with 70% ethanol and used as is. Toxicity of residual starting materials leaching from PCLF scaffolds was evaluated using a non contact method. PC12 cells were seeded in 12-well plates at a density of 20,000 cells $cm^{-2}$ for 24 hours prior to the addition of the polymeric material contained in transwells. PC12 cells were cultured in the presence of polymeric materials for 1 day, and then the cell numbers were quantified with an MTS assay and the transwells were transferred to fresh wells containing cells and cultured for another 3 and 7 days.

To investigate PC12 cell response to different polymeric materials, 1.0 cm disks were placed in 24-well plates. The scaffolds were sterilized in 70% aqueous ethanol for 30 minutes and then rinsed with sterile phosphate buffered saline (PBS). Autoclaved medical grade silicon tubing was inserted into the well to limit the surface area of the polymer disk to a diameter of 0.95 cm with a surface area of 0.71 $cm^2$. The well was filled with media and incubated for 12 hours to remove any remaining impurities. PC12 cells were plated at a density of 30,000 cells $cm^{-2}$. Experiments were performed with nerve growth factor (NGF; 50 ng $mL^{-1}$) supplemented media.

Cell viability was determined using MTS (Promega, Madison, Wis.) assays. First, 0.5 mL trypsin was added to each well, aspirated, and put in the incubator for 10 minutes. Then 0.5 mL media was added to each well, and cells were gently dislodged from the surface with a cell scraper. Media and cells were then transferred to a new well and 0.1 mL of MTS (3-(4,5-dimethylthiazol-2-yl)-5-(3-carboxymethoxyphenyl)-2-(4-sulfophenyl)-2H-tetrazolium) reagent was added to each well then and incubated for 2 hours at 37° C. The absorbance was measured at 490 nm on a Molecular Devices spectra max plate reader.

Cell morphology was imaged by fluorescence microscopy. PC12 cells on polymer scaffolds were fixed in 2% parafomaldehyde in PBS for 25 minutes, and then washed with PBS three times. Cells were permeablized in 0.1% Triton 100× surfactant for 3 minutes and then incubated in 10% horse serum in PBS for 1 hour. Cells were stained in 1% rhodium phalloidin in 5% horse serum in PBS for 1 hour and then washed with PBS three times. Nuclei were stained with DAPI (4',6-diamidino-2-phenylindole) just prior to mounting on a glass cover slip. Samples were imaged on an LSM 510 inverted confocal microscope and imaged at excitation wavelengths of 368 and 488 nm. See FIGS. 11, 11A, 11B, 11C, 11D, 11E, and 11F which show PC12 cell attachment and morphology.

II. Results

A. Synthesis of Polycaprolactone and Polycaprolactone Fumarate Polymers

Polycaprolactone precursor polymers were synthesized from 1,2 propane diol or glycerol initiators with a monomer:

initiator ratio of 19:1. This ratio was chosen in order to synthesize polycaprolactone with molecular weights similar to the commercially available polycaprolactone ether diol synthesized from diethylene glycol (DEG). The polycaprolactone precursors were analyzed by GPC to ensure similar molecular weights.

One polycaprolactone fumarate polymer ($PCLF_{PPD}$) was produced by reacting fumaryl chloride with polycaprolactone precursor polymers synthesized from 1,2 propane diol ($PCL_{PPD}$). Another polycaprolactone fumarate polymer ($PCLF_{GLY}$) was produced by reacting fumaryl chloride with polycaprolactone precursor polymers synthesized from glycerol ($PCL_{GLY}$). Yet another polycaprolactone fumarate polymer ($PCLF_{DEG}$) was produced by reacting fumaryl chloride with polycaprolactone precursor polymers synthesized from diethylene glycol ($PCL_{DEG}$). FIG. 2 shows synthetic schemes of $PCLF_{PPD}$ and $PCLF_{GLY}$.

Figure 3:
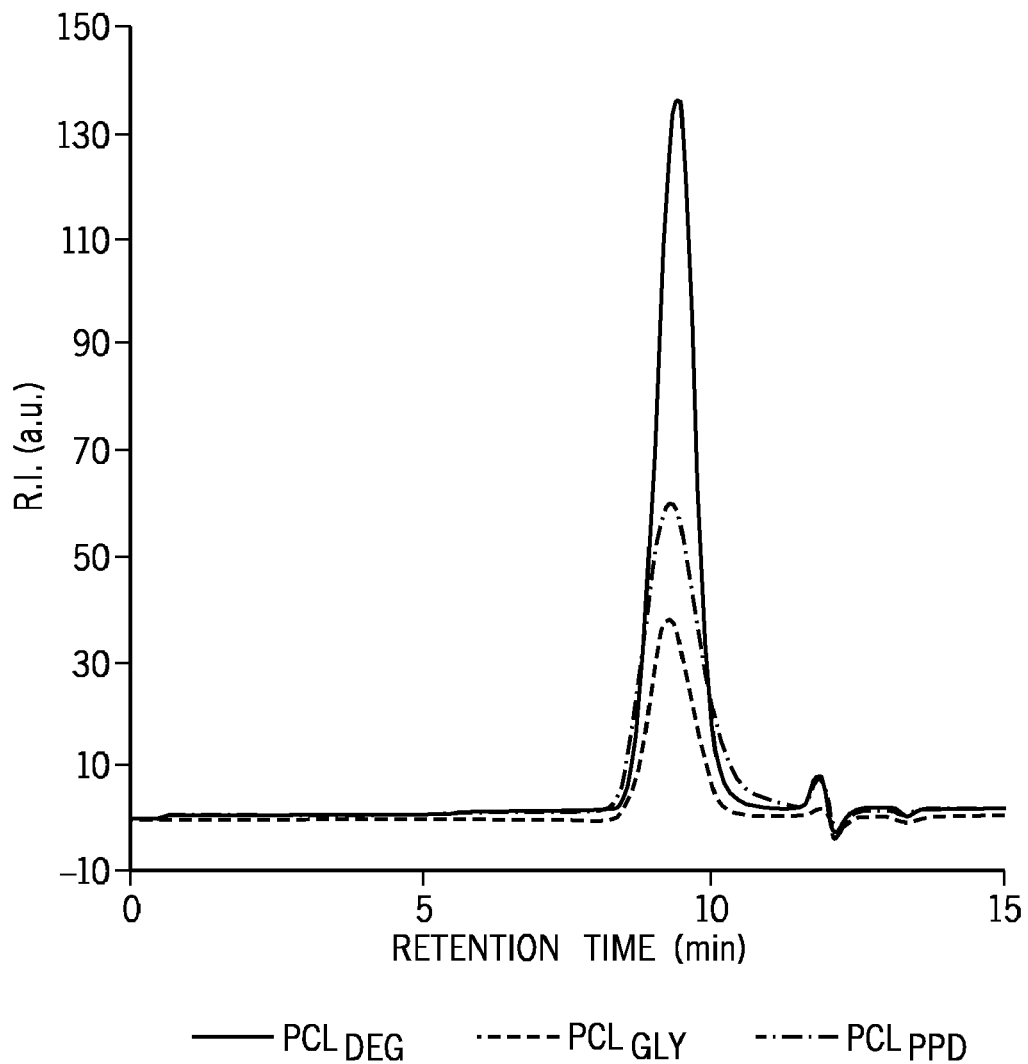
FIG. 3 shows a GPC trace of a polycaprolactone precursor polymer synthesized from 1,2 propane diol (PCL$_{PPD}$), a polycaprolactone precursor polymer synthesized from glycerol (PCL$_{GLY}$), and a polycaprolactone precursor polymer synthesized from diethylene glycol (PCL$_{DEG}$).
Figure 4A:
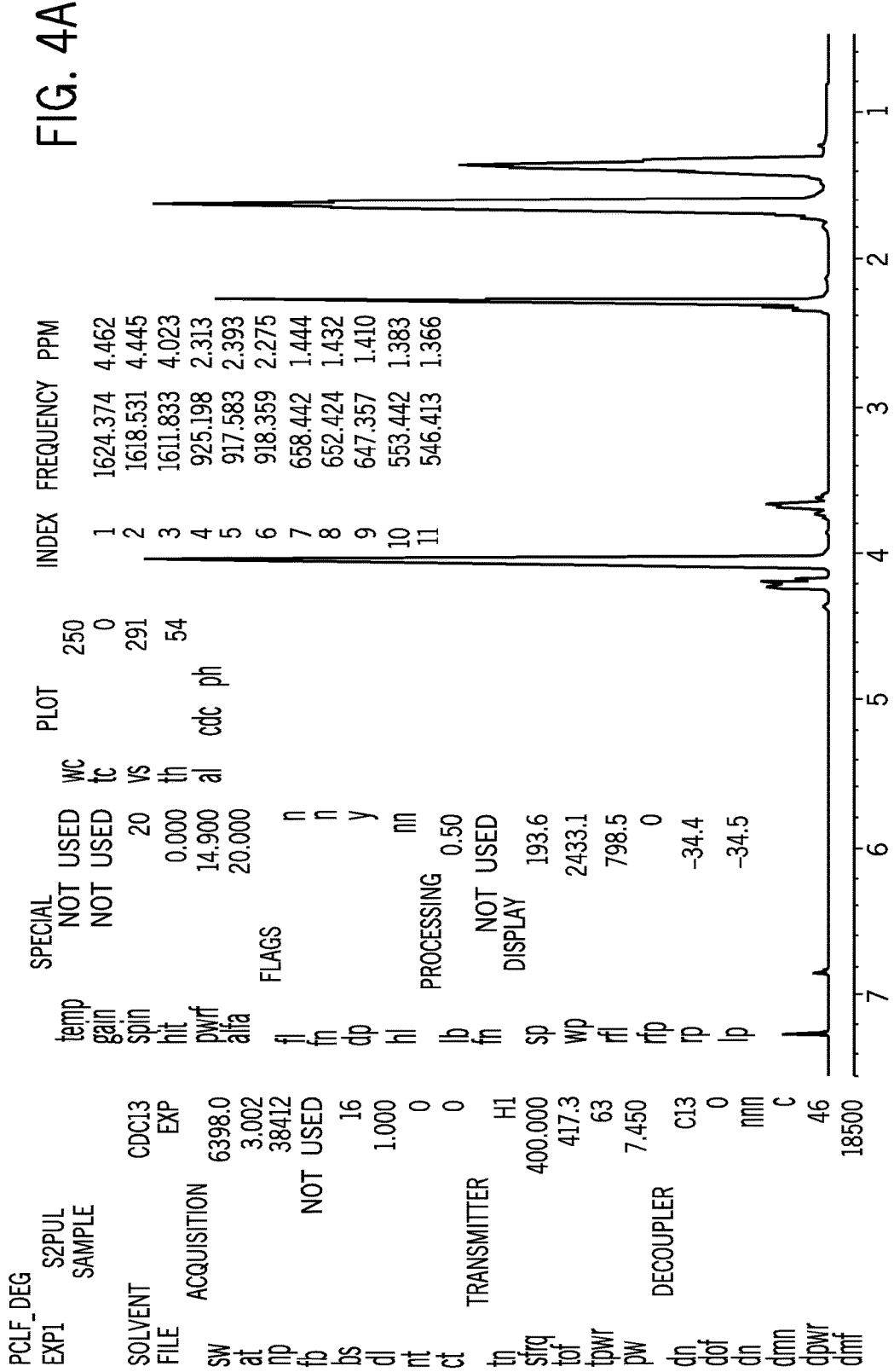
FIG. 4 shows an H NMR of PCL$_{PPD}$, PCL$_{GLY}$, PCLF, PCLF$_{PPD}$, and PCLF$_{GLY}$.
Figure 4B:
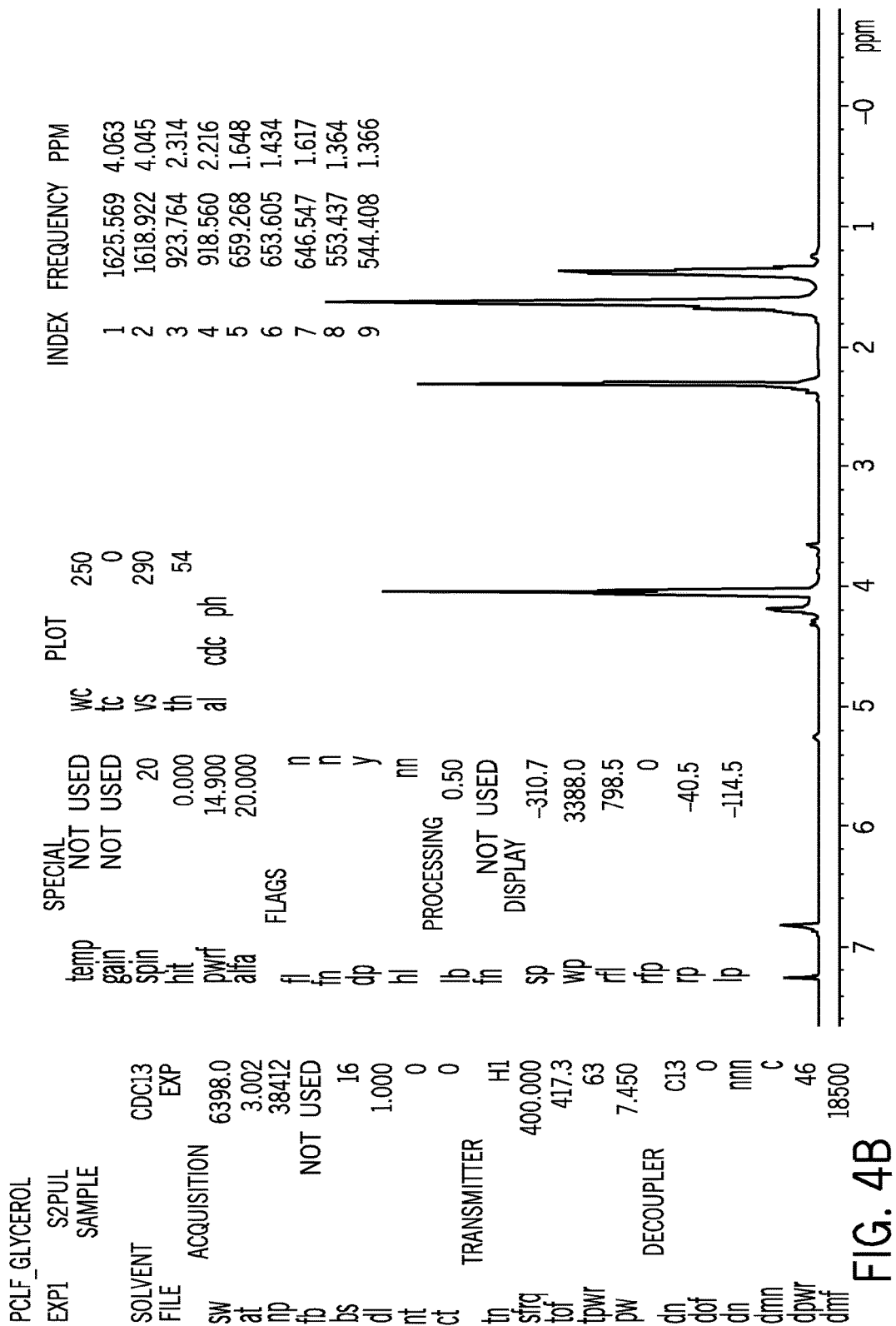
Figure 4C:
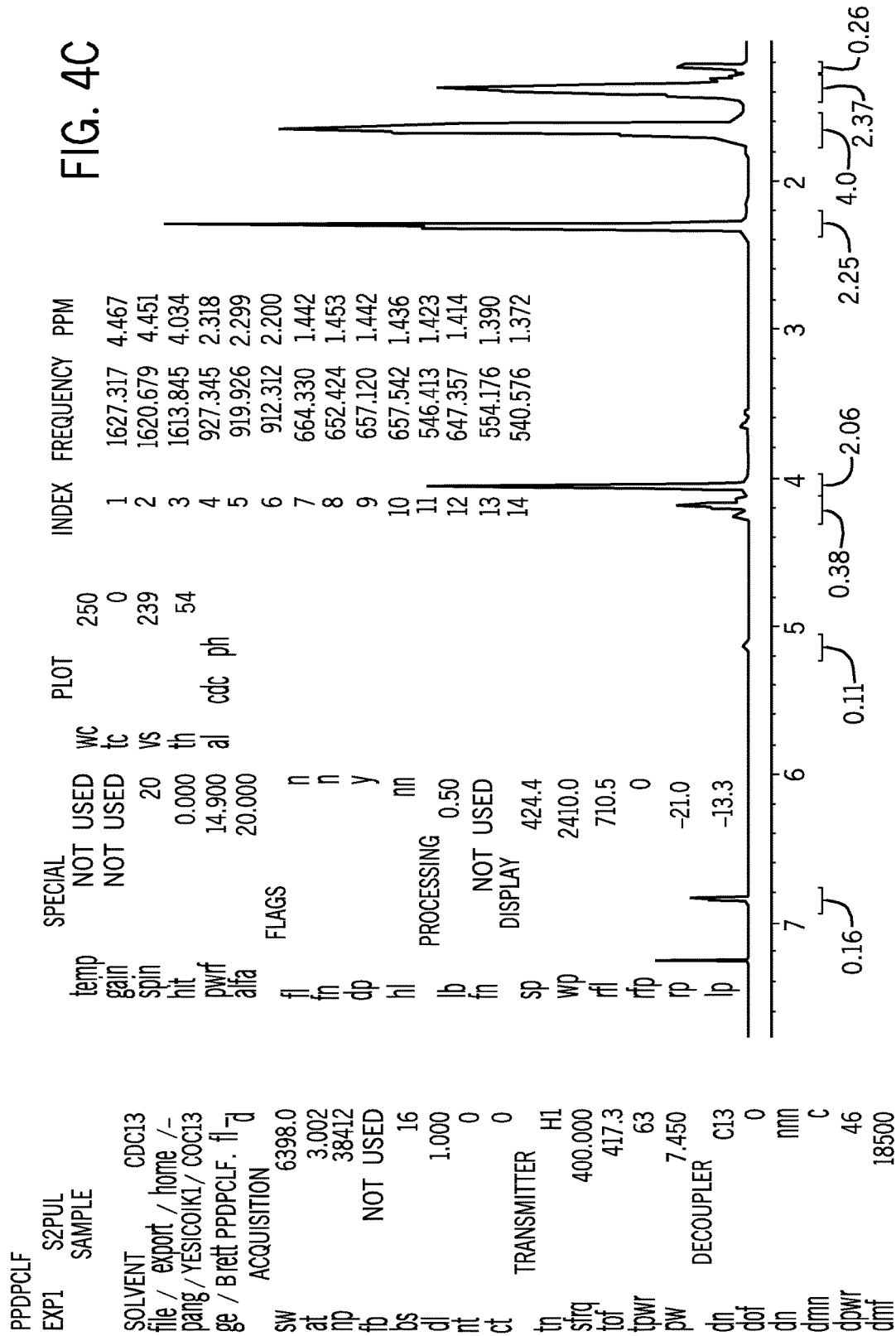
Figure 4D:
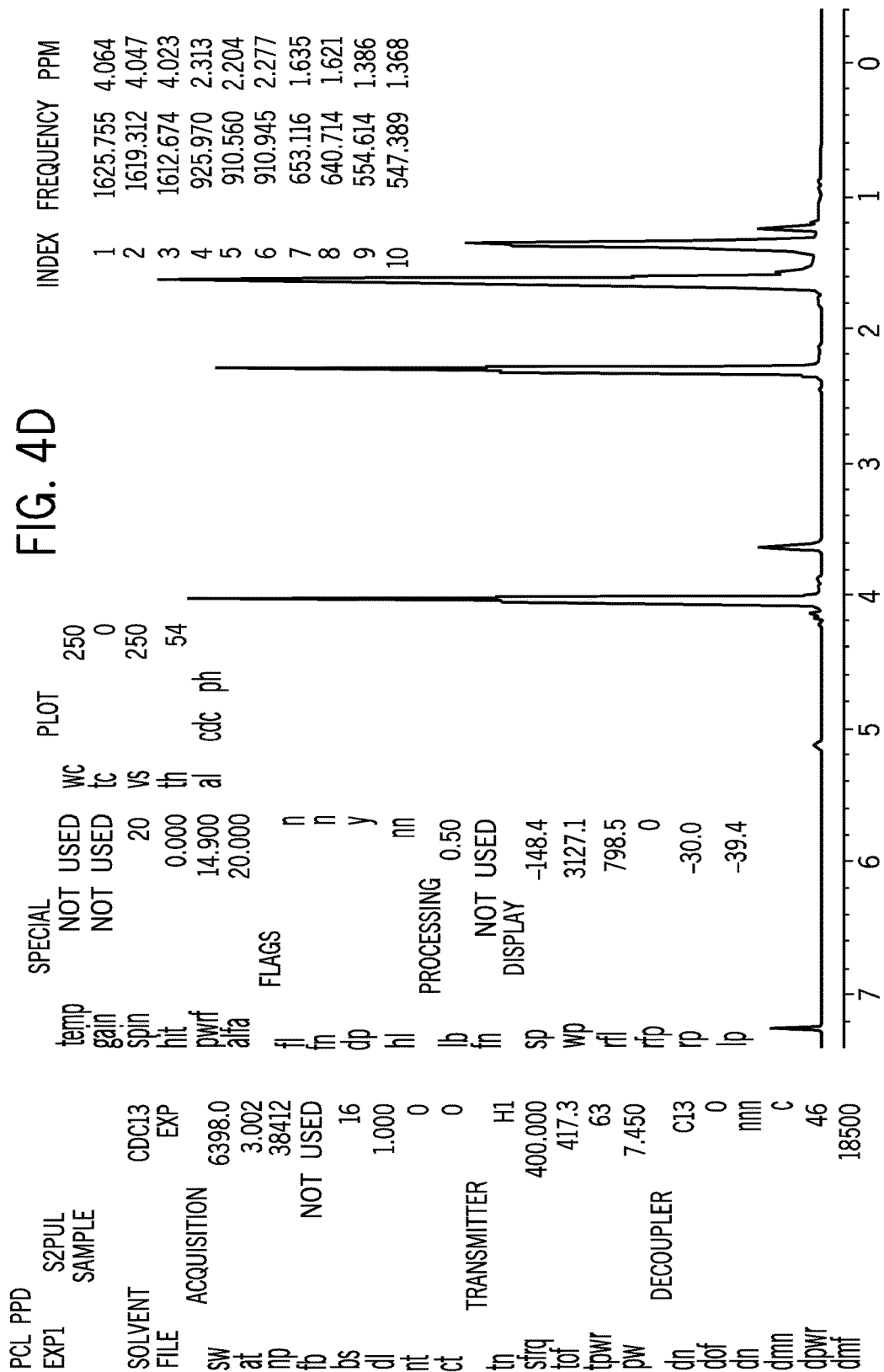
Figure 4E:
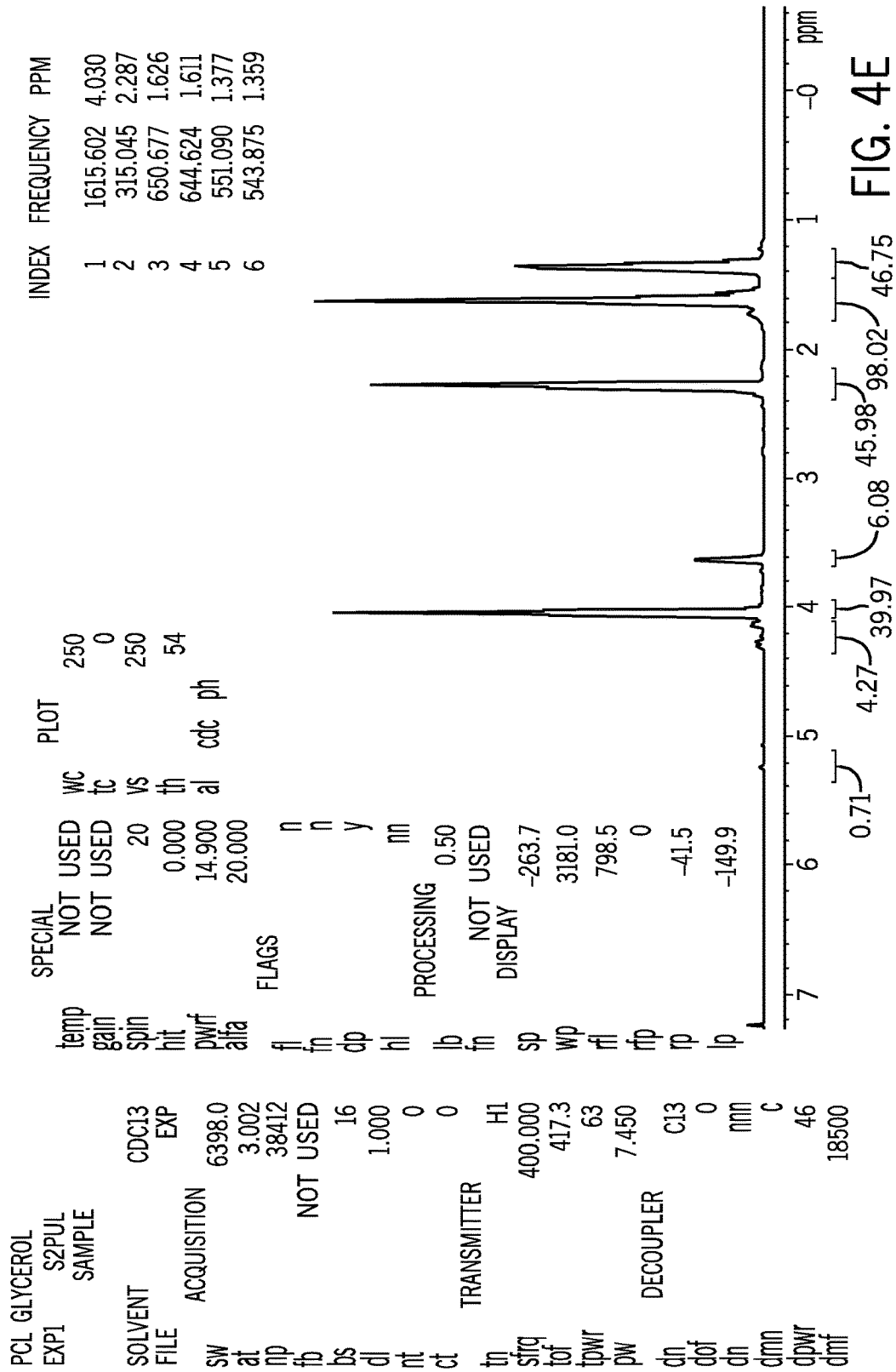

FIG. 3 shows that the GPC traces for polycaprolactone polymers are all symmetrical and nearly identical. The polycaprolactone molecular weights determined by GPC are shown in Table 1 below. The molecular weights for the synthesized PCL and commercially available PCL are very similar indicating all of the caprolactone was consumed during the PCL synthesis.

TABLE 1

Molecular Weight Characterization

| [a]Polymer | [b]Predicted $M_w$ (g mol$^{-1}$) | [c]$M_n$ (g mol$^{-1}$) | PDI $M_w/M_n$ | [d] $^1$H NMR (g mol$^{-1}$) |
|---|---|---|---|---|
| $PCL_{DEG}$ | 2000 | 3800 | 1.7 | 2308 |
| $PCL_{PPD}$ | 2245 | 3500-4400 | 1.4 | 2176 |
| $PCL_{GLY}$ | 2260 | 4000-5500 | 1.3 | 2386 |
| $PCLF_{DEG}$ | — | 11190 | 1.9 | — |
| $PCLF_{PPD}$ | — | 12200 | 2.0 | — |
| $PCLF_{GLY}$ | — | 10100 | 2.7 | — |

Characterization of polymer molecular weights.
[a]The polymer composition described as polymer$_{initiator}$.
[b]The predicted molecular weight based on monomer: initiator loading or the molecular weight given by commercial source.
[c]Number average molecular weight measured by GPC using polystyrene standards.
[d] Molecular weight determined by endgroup analysis.

End group analysis using the terminal $CH_2$—OH groups present in $^1$H NMR of the polycaprolactone polymers indicate the polycaprolactone molecular weights are also very close to the desired $M_n$ of 2000 g mol$^{-1}$. The $^1$H NMR protons associated with the initiator moieties are visible after the polycaprolactone synthesis and have shifted from 3.3 and 3.8 to 4.15, 4.28 and 5.25 for $PCL_{GLY}$ and 3.5 and 3.8 to 4.15 and 5.15 for $PCL_{PPD}$ indicating that initiation of polycaprolactone from both the primary and secondary alcohols occurred on the PPD and GLY initiators. The discrepancy between molecular weights determined by GPC and end group analysis is caused by the use of polystyrene standards for generation of the GPC calibration curve.

Because of the different architecture and the increased number of alcohols on $PCL_{GLY}$, reaction times varied. Reactions with $PCL_{PPD}$ were refluxed for 12 hours, while reactions using $PCL_{GLY}$ were monitored by GPC and a typical reaction time was 5 hours. All PCLF architectures had similar molecular weights ranging from 10-12 kg mol$^{-1}$ for this study. However, $PCLF_{GLY}$ had a broader PDI of 2.9.

B. Characterization of Thermal Transitions and Crystalline Properties

Figure 5:
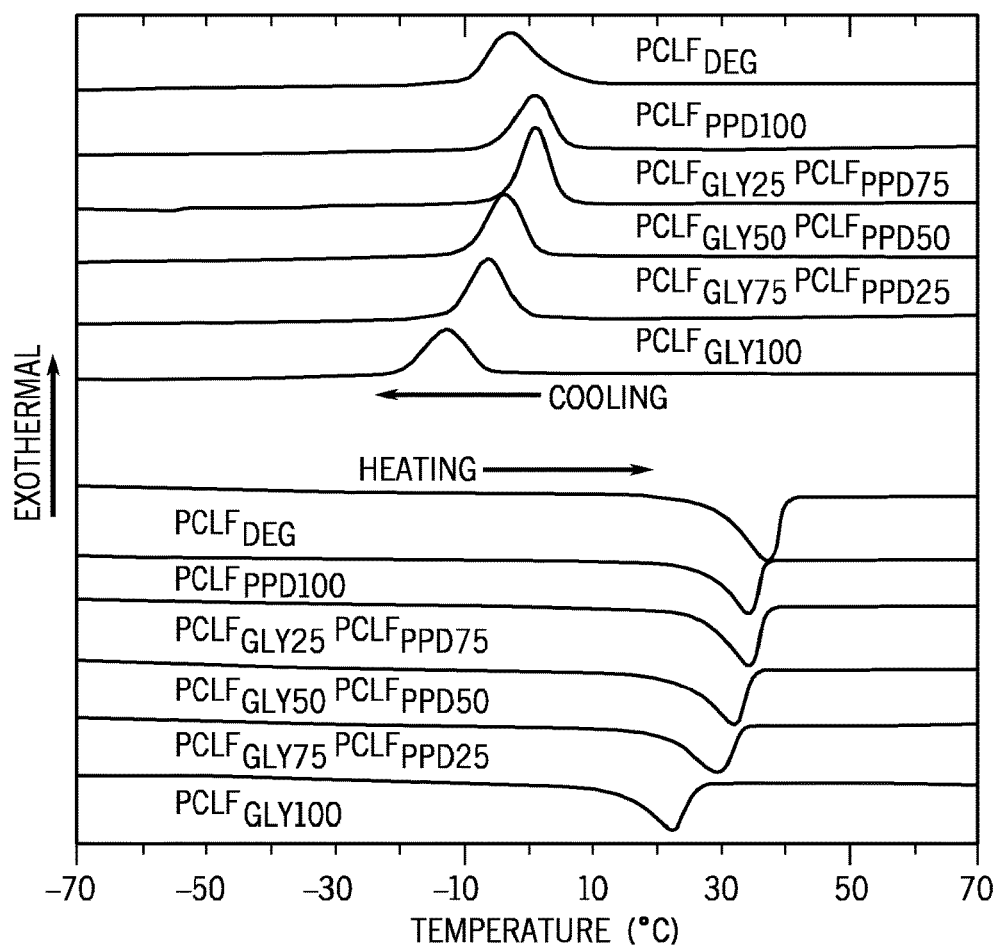
FIG. 5 shows a differential scanning calorimetry showing the heating and cooling traces of different PCLF compositions.

In order investigate the material properties of the new cross-linked polycaprolactone fumarate scaffolds, compositions of $PCLF_{GLY}$ and $PCLF_{PPD}$ ranging from 0 to 100 wt. % were fabricated. The thermal, swelling, mechanical, and rheological properties were characterized and compared with previously studied $PCLF_{DEG}$. FIG. 5 shows the heating and cooling traces from differential scanning calorimetry (DSC) experiments used to measure the thermal transitions of PCLF. $T_m$, $T_c$, $T_g$, $\Delta H_m$, $\Delta H_c$, and % crystallinity were analyzed and the results are shown in Table 2 below.

TABLE 2

Thermal properties

| Polymer Composition | Tg (° C.) | Tm (° C.) | Tc (° C.) | ΔHm J/g | ΔHc J/g | Percent Crystallinity |
|---|---|---|---|---|---|---|
| $PCLF_{DEG}$ | −55.8 | 37.2 | −3.4 | 42.1 | 41.7 | 31.2 |
| $PCLF_{PPD100}$ | −56.8 | 34.5 | 1.1 | 40.5 | 39.4 | 29.9 |
| $PCLF_{PPD75}PCLF_{GLY25}$ | −57.7 | 34.3 | 1 | 39 | 39.9 | 28.9 |
| $PCLF_{PPD50}PCLF_{GLY50}$ | −57.1 | 32.04 | −3.5 | 36.9 | 36.5 | 27.3 |
| $PCLF_{PPD25}PCLF_{GLY75}$ | −56.7 | 29.8 | −6.4 | 35.1 | 34.7 | 26 |
| $PCLF_{GLY100}$ | −56.3 | 22.4 | −13.2 | 33.1 | 32.5 | 24.5 |

In the polymer compositions of Table 2, $PCLF_{DEG}$ was 100 wt. % $PCLF_{DEG}$; $PCLF_{PPD100}$ was 100 wt. % $PCLF_{PPD}$; $PCLF_{PPD75}$ $PCLF_{GLY25}$ was 75 wt. % $PCLF_{PPD}$ and 25 wt. % $PCLF_{GLY}$; $PCLF_{PPD50}PCLF_{GLY50}$ was 50 wt. % PCLF-PPD and 50 wt. % $PCLF_{GLY}$; $PCLF_{PPD25}$ $PCLF_{GLY75}$ was 25 wt. % $PCLF_{PPD}$ and 75 wt. % $PCLF_{GLY}$; and $PCLF_{GLY}$ was 100 wt. % $PCLF_{GLY}$.

Figure 6A:
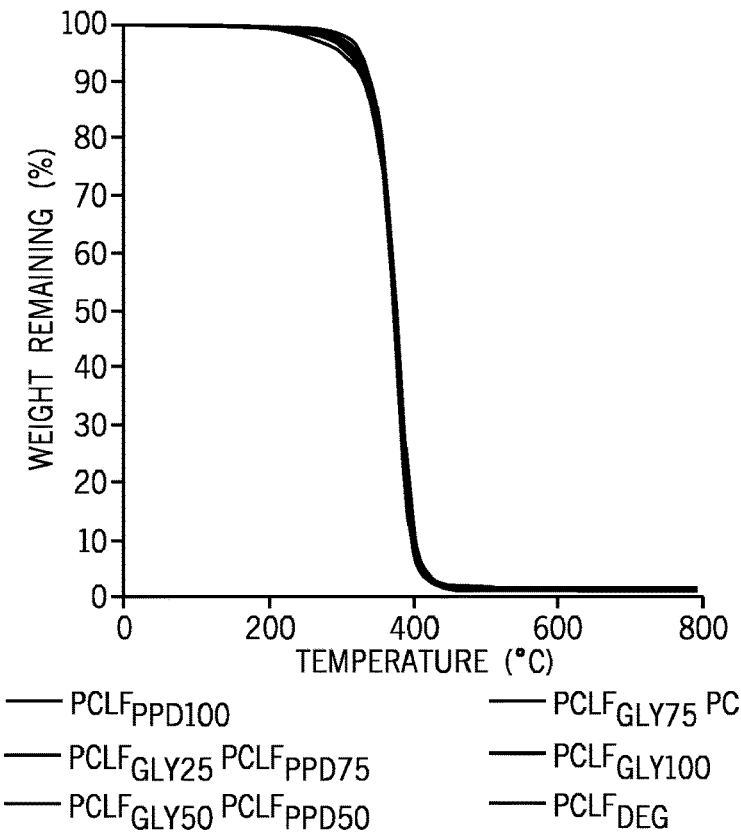
FIG. 6 shows a thermogravimetric analysis showing the thermal decomposition with increasing temperature of cross-linked PCLF scaffolds.
Figure 6B:
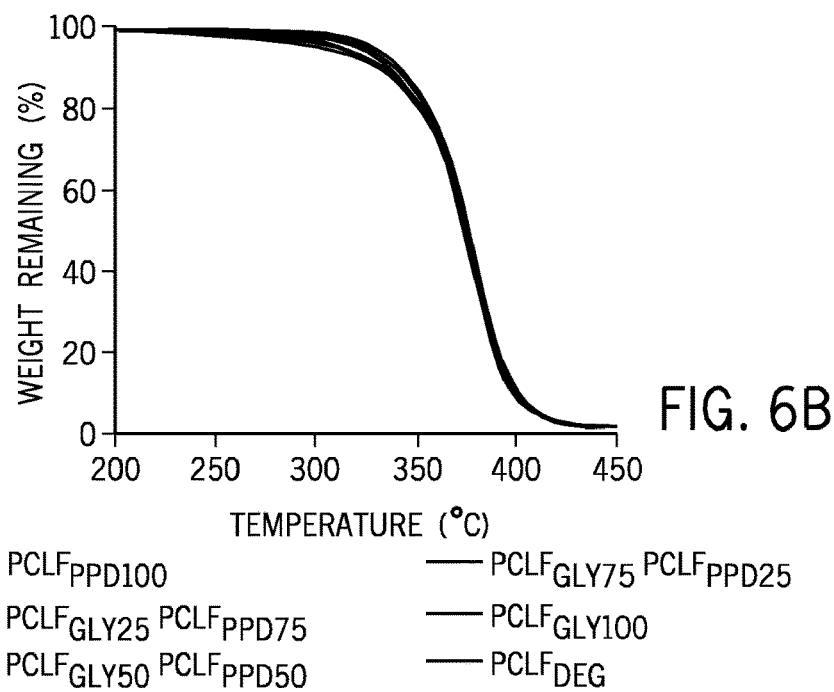

The DSC data shows that $PCLF_{PPD}$ exhibits thermal and crystalline properties very similar to $PCLF_{DEG}$. Compared to $PCLF_{DEG}$, $PCLF_{GLY}$ possesses a lower $T_m$ from 37.2° C. to 22.4° C., reduced crystallinity from 31.2% to 24.5%, and decreased $\Delta H_m$ from 42.1 to 33.1 J/g. Table 2 also shows that the $T_m$, $T_c$, $\Delta H_m$, $\Delta H_c$, and % crystallinity can be tuned by choice of $PCLF_{PPD}PCLF_{GLY}$ blend composition. FIG. 6 shows the thermal decomposition of the various PCLF scaffolds. All scaffolds show similar onsets of decomposition occurring at nearly 200° C. This indicates that the polymers are thermally stable at temperatures of 121° C. to 134° C. typically used for autoclave.

C. Swelling Ratio

Figure 7:
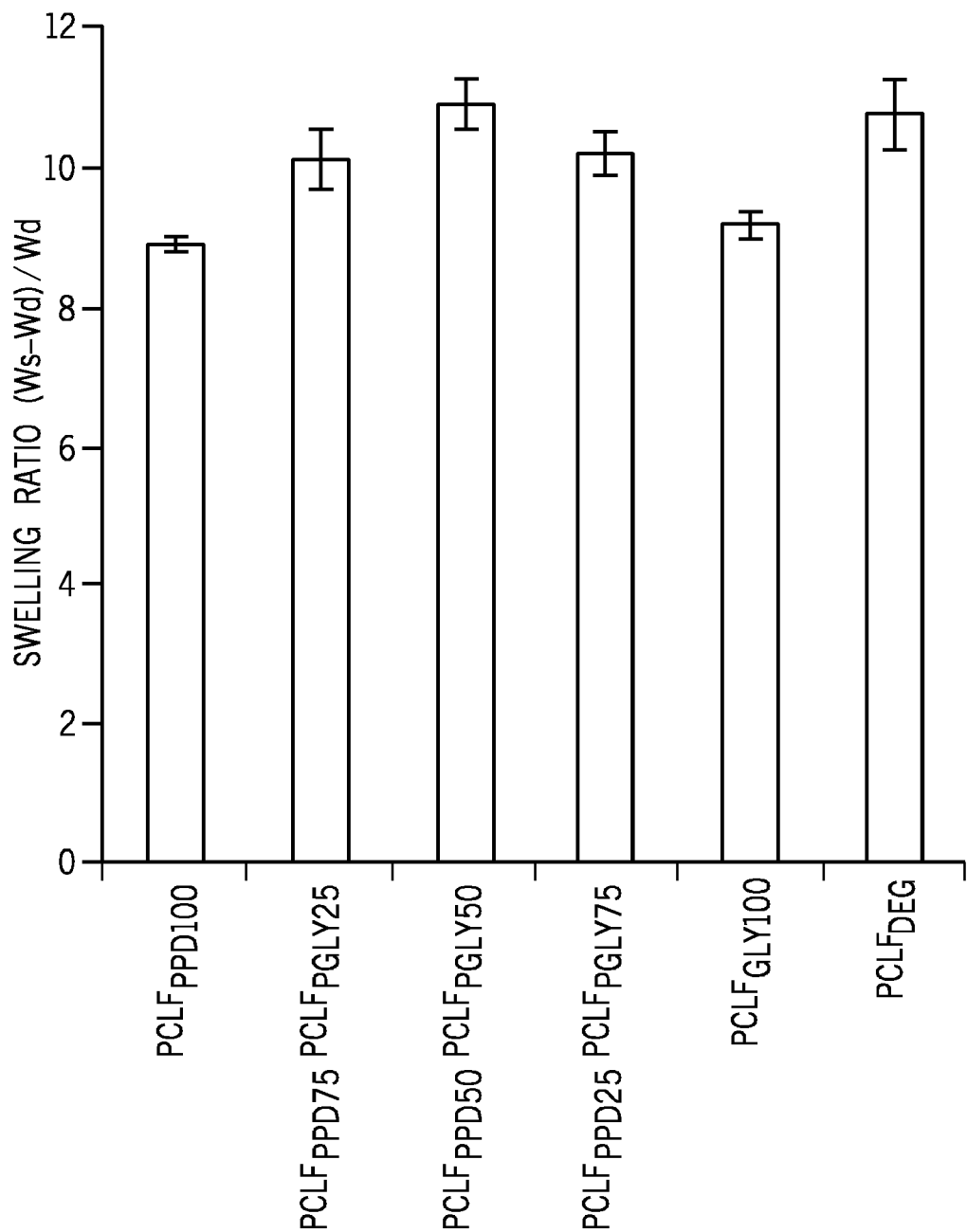
FIG. 7 shows the swelling ratio of PCLF scaffolds in methylene chloride. The swelling ratio was determined by the equation (Ws−Wd)Wd, where Ws is swollen weight and Wd is dry weight.

The swelling ratio of cross-linked polymeric films is an indicator of the relative cross-link density. The more highly cross-linked a material is the less swelling occurs when placed in a theta solvent. FIG. 7 shows the small differences in the swelling ratio of cross-linked polycaprolactone fumarate. $PCLF_{DEG}$ has the highest swelling ratio indicating the lowest cross-linking density. Interestingly, the $PCLF_{PPD50}PDLF_{GLY50}$ has the a similar swelling ratio, while both $PCLF_{PPD}$ and $PCLF_{GLY}$ have similar low swelling ratios indicating a higher cross-link density.

D. Mechanical Properties

Figure 8A:
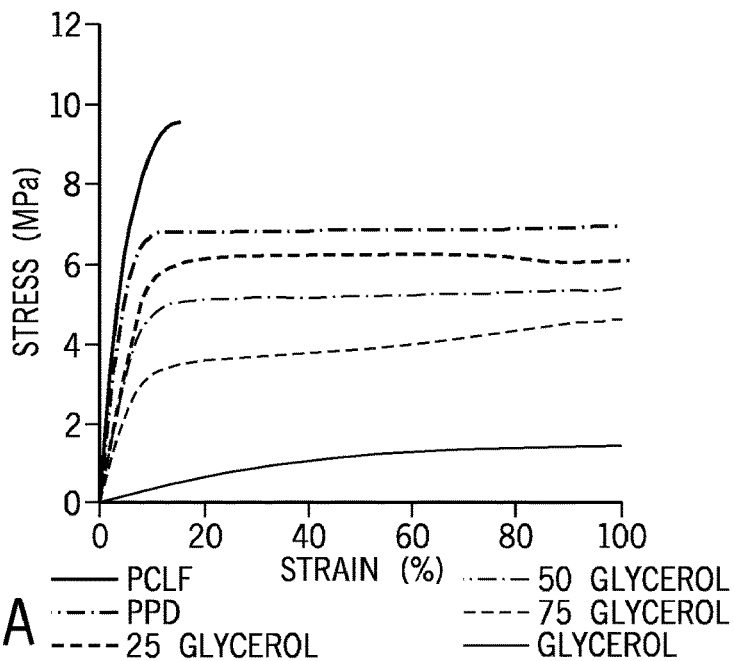
FIG. 8A shows a stress-strain curve for different PCLF compositions.
Figure 8B:
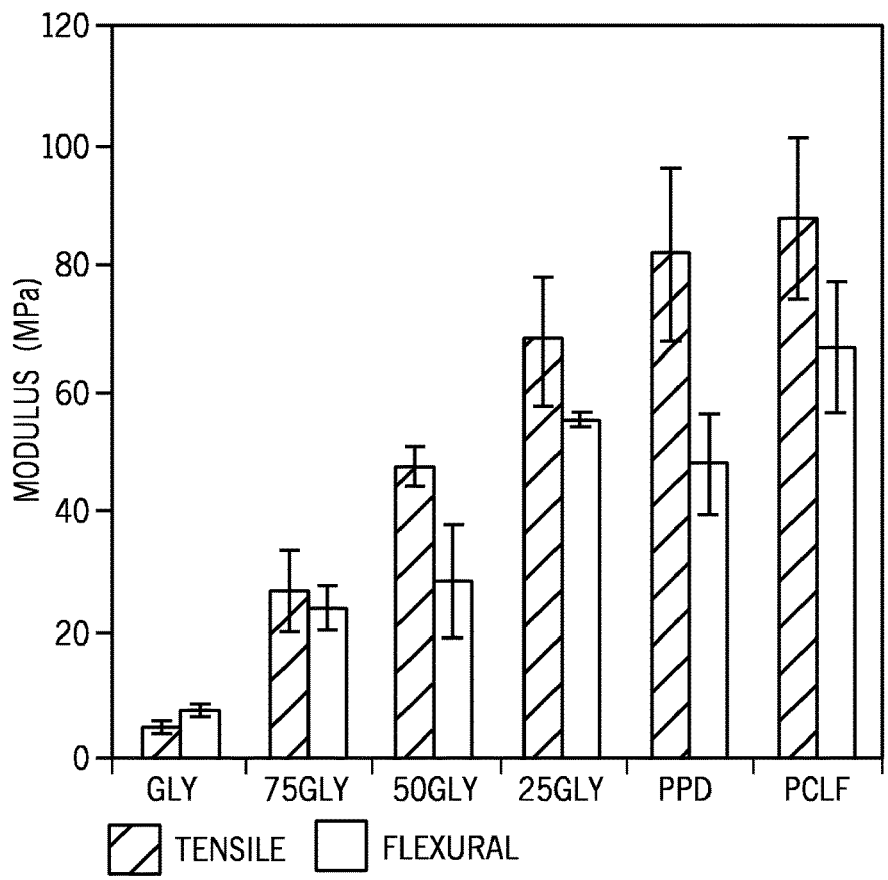
FIG. 8B shows tensile and flexural modulus for different PCLF compositions.

The presence and percent of crystalline regions in polymer scaffolds greatly affects the scaffold mechanical properties, typically increasing the crystallinity will increase a material's mechanical strength. Because of the differences in the crystalline properties of $PCLF_{GLY}$, $PCLF_{PPD}$, and $PCLF_{DEG}$, the flexural and tensile modulus were measured. FIG. 8A shows the stress strain plots of the PCLF materials in stretching mode. The stress strain plot shows the distinctly different nature of the polymeric materials. PCLF$_{DEG}$, and formulations containing any amount of PCLF$_{PPD}$, exhibit rubber-like properties with reversible elastic properties at low strains <20%. PCLF$_{GLY100}$ stress strain curve resembles an elastomeric material with high strains under low stress. The results of the tensile and flexural moduli measurements at 5% strain are shown in FIG. 8B. PCLF$_{DEG}$ has tensile and flexural moduli of 88±13 and 67±10 MPa respectively. PCLF$_{PPD}$ exhibits slightly decreased moduli 55±4 and 47±8 while PCLF$_{GLY}$ shows significantly lower tensile and flexural moduli of 4±1 and 7±1 MPa respectively. PCLF$_{GLY}$ and PCLF$_{PPD}$ blends moduli increased with increasing percentage of PCLF$_{PPD}$.

E. Rheological Properties

Figures 9A, 9B:
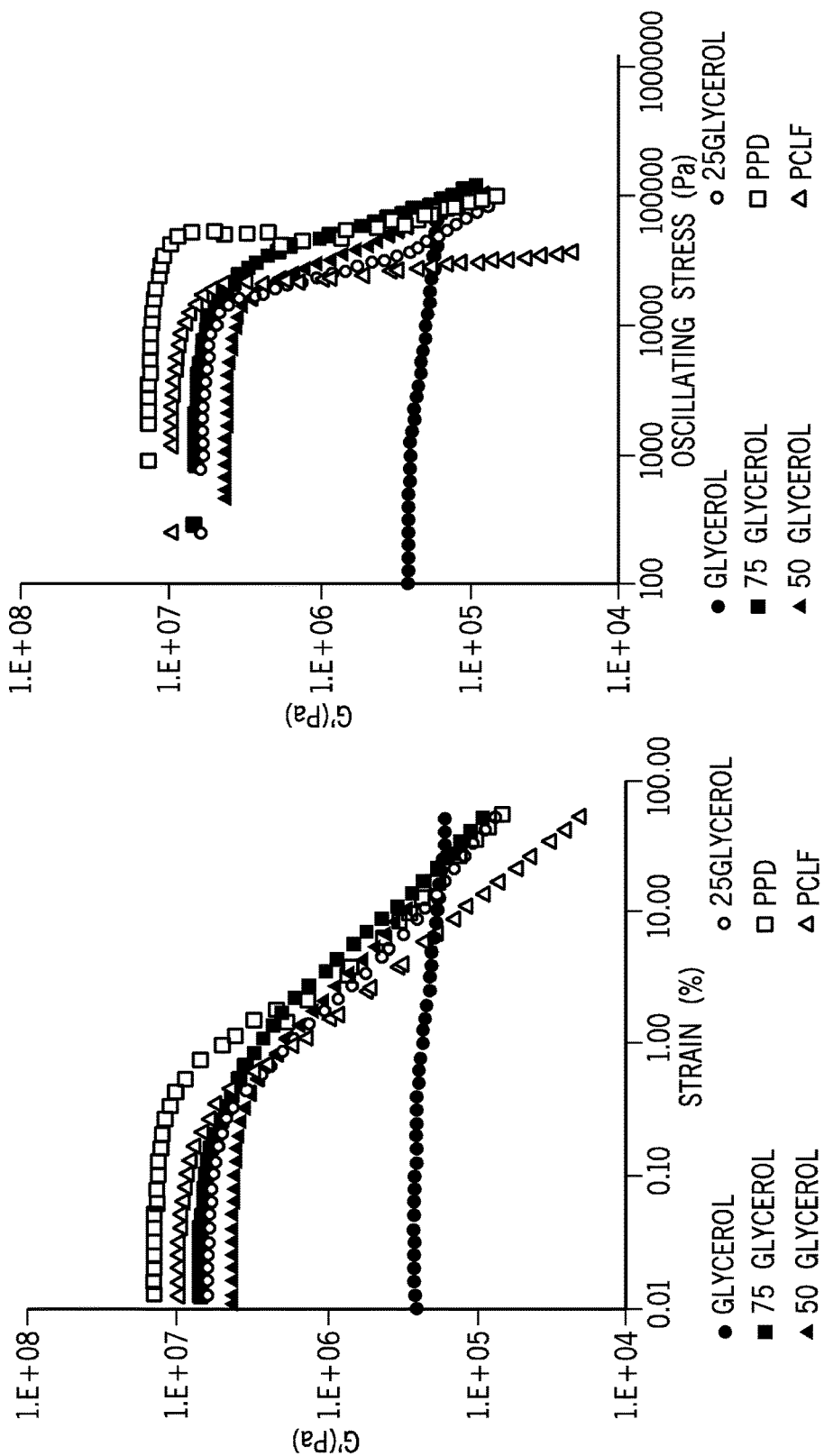
FIG. 9A shows rheological measurements for % strain for different PCLF compositions.
FIG. 9B shows rheological measurements for oscillating stress for different PCLF compositions.
Figure 9F:
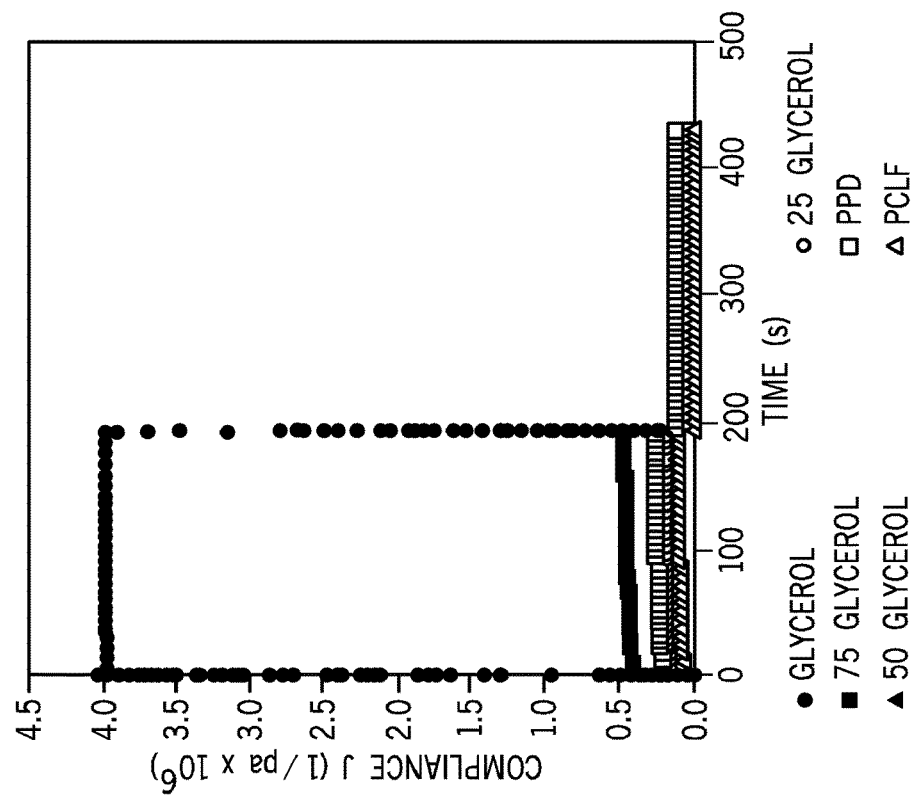
FIG. 9F shows rheological measurements for creep and recovery of PCLF films with an applied stress of 10 kPa for different PCLF compositions.
Figure 9E:
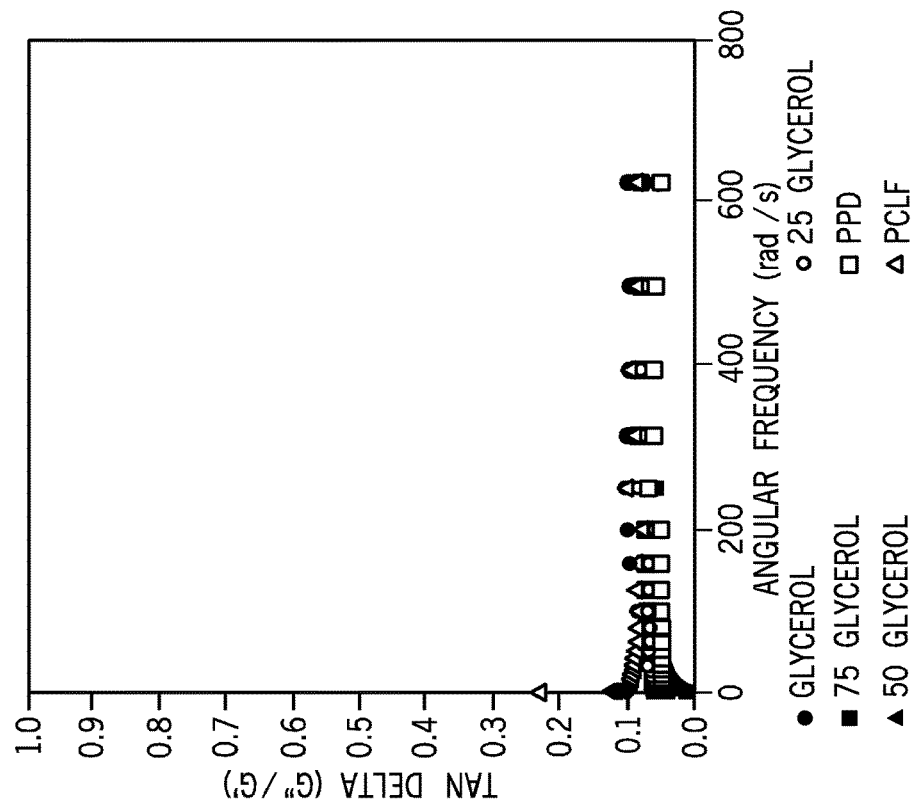
FIG. 9E shows rheological measurements for tan δ as a function of frequency for different PCLF compositions.

Rheology was used to analyze the viscoelastic properties of the different polycaprolactone fumarate materials and subsequent blends. Frequency sweep and creep experiments were used to measure the storage and loss moduli as well as the materials' compliance and recovery behavior. These parameters were used to investigate the effects of the different crystalline microstructure on the cross-linked polycaprolactone fumarate viscoelastic behavior and were also used to evaluate material changes after autoclave sterilization. The linear elastic regions of PCLF materials were determined by performing strain sweeps from 0.1 to 100% strain at a frequency of 1 Hz. The linear region where G' is independent of strain (FIG. 9A) or oscillating stress (FIG. 9B) were used to determine overlapping linear viscoelastic regions. All frequency sweeps were performed at 0.05% strain and the storage modulus (G') and loss modulus (G") vs. frequency are shown in FIGS. 9A and 9D for all PCLF compositions. G' was measured at the physiologically relevant 37° C. and is shown to be independent of frequency for all PCLF materials. PCLF$_{DEG}$ and PCLF$_{PPD}$ have the highest G' of 14.7 and 12.4 MPa respectively at 100 rad/s. G' decreases with increasing amounts of PCLF$_{GLY}$ to 3.7 MPa for PCLF$_{PPD25}$PCLF$_{GLY75}$, and PCLF$_{GLY100}$ has a G' of 0.3 MPa, over an order of magnitude lower than all other compositions. G" exhibits frequency dependent behavior for PCLF$_{GLY}$, but is mainly independent for all other PCLF compositions. G" measurements are an order of magnitude lower than G', and this relationship is plotted as tan δ in FIG. 9E. Tan δ can be used to evaluate a materials elasticity and is plotted as G"/G' vs. frequency. FIG. 9E shows all PCLF materials have tan δ values around 0.1 indicating the materials exhibit similar elastic behavior despite the differences in G' and G" values.

In order to further demonstrate differences in the material properties of the branched vs. linear PCLF scaffolds, a creep experiment was performed to illustrate the compliance and recovery properties. The creep experiments shown in FIG. 9F demonstrate that the materials possess distinctly different compliance characteristics when a constant stress of 10 kPa applied. PCLF$_{DEG}$ and PCLF$_{PPD}$ exhibited shear strains of 0.11-0.27%. These strains are 1/36-1/14 of the 4.0% shear strain experienced by PCLF$_{GLY100}$.

F. Autoclave Sterilization

Sterilization is critical for translation of biomaterials into a clinical product. Because autoclave sterilization is a quick, effective, and FDA approved sterilization method, the effect of the autoclave process on the PCLF properties was examined. A standard autoclave procedure was used with a temperature of 123° C. for 23 minutes in the presence of steam. Immediately after autoclave sterilization, all materials appear transparent and slowly turned opaque as the scaffolds cooled. The three-dimensional structure was maintained and no noticeable changes in the scaffold were observed. In order to determine material changes, the PCLF thermal and rheological properties were characterized and compared with the properties prior to autoclave treatment. Table 3 below shows the DSC results and changes in thermal transitions for PCLF materials after autoclave.

TABLE 3

Effect of Autoclave Sterilization on Thermal Properties

| Polymer Composition | Tg (° C.) | Tm (° C.) | Tc (° C.) | ΔHm J/g | ΔHc J/g | Percent Crystallinity |
|---|---|---|---|---|---|---|
| PCLF$_{DEG}$ | −57.2 | 39.4 | 12.93 | 49.7 | 50.2 | 36.8 |
|  | (−1.4) | (2.2) | (16.3) | (7.6) | (8.5) | (5.6) |
| PCLF$_{PPD100}$ | −58.2 | 37.7 | 9.3 | 43.9 | 45.6 | 32.5 |
|  | (−1.4) | (3.2) | (8.2) | (3.4) | (6.2) | (2.6) |
| PCLF$_{PPD75}$ PCLF$_{GLY25}$ | −58.6 (−0.9) | 36.7 (2.4) | 9.6 (−8.6) | 46.7 (7.7) | 44.4 (4.5) | 34.6 (5.7) |
| PCLF$_{PPD50}$ PCLF$_{GLY50}$ | −57.5 (−0.4) | 33.7 (1.7) | 5.1 (−8.6) | 38.1 (1.2) | 39.3 (2.8) | 28.2 (0.9) |
| PCLF$_{PPD25}$ PCLF$_{GLY75}$ | −57.1 (−0.4) | 31.9 (2.1) | 5.1 (−11.5) | 41.7 (6.6) | 41.5 (6.8) | 30.9 (4.9) |
| PCLF$_{GLY100}$ | −56.8 | 24 | 8.2 | 34.1 | 33.1 | 25.3 |
|  | (−0.5) | (1.6) | (5.0) | (1.0) | (0.6) | (0.8) |

The glass transitions decreased by 0.4-1.4° C., the melting temperatures increased 1.6-3.2° C., and the crystallization temperatures increased from 5.0-16.3° C. The percent crystallization, ΔHm, and ΔHc increases ranged from 0.8-5.6%, 1.0-7.7 J/g, and 0.6-8.5 J/g respectively. For all parameters, PCLF$_{GLY}$ consistently exhibited the lowest change due to the autoclave sterilization process.

Figures 10A, 10B:
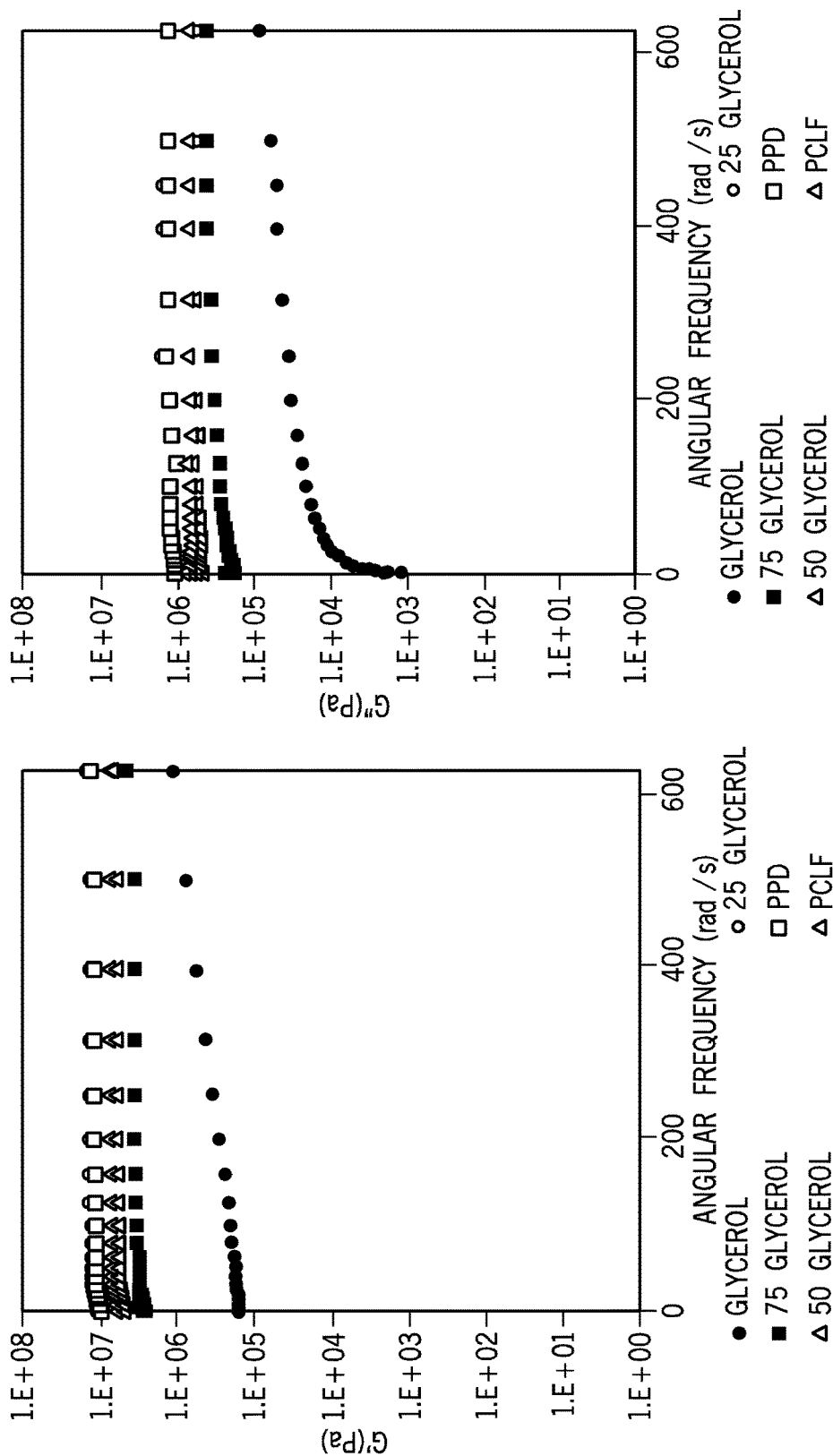
FIG. 10A shows rheological measurements for storage modulus for different PCLF compositions after autoclave sterilization.
FIG. 10B shows rheological measurements for loss modulus for different PCLF compositions after autoclave sterilization.
Figure 10D:
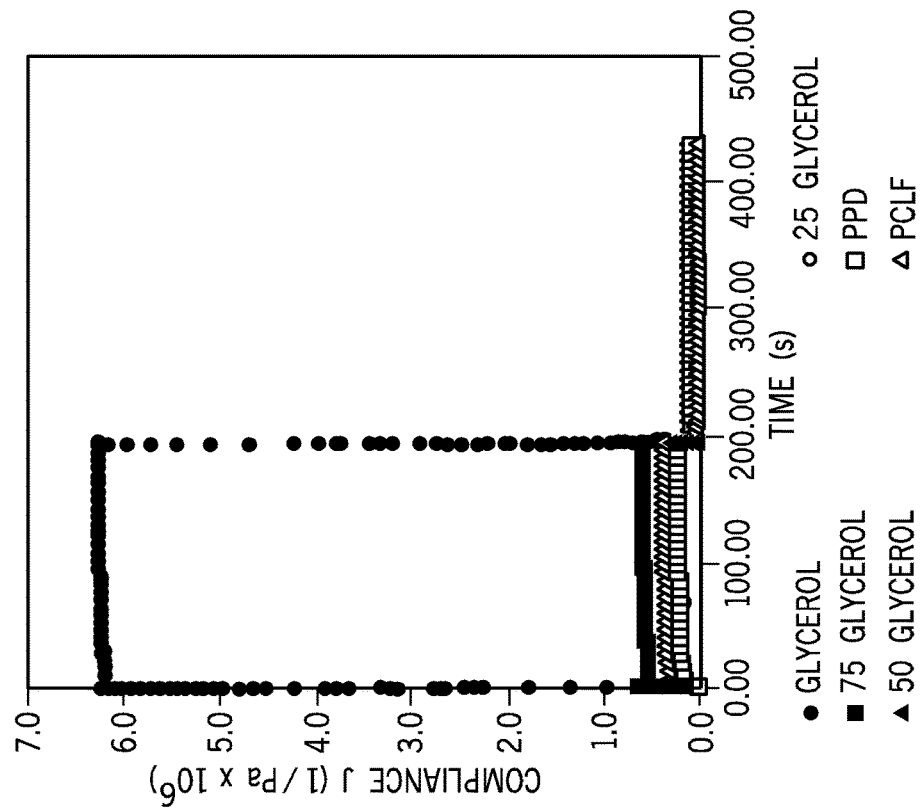
FIG. 10D shows rheological measurements for creep and recovery of PCLF films with an applied stress of 10 kPa for different PCLF compositions after autoclave sterilization.
Figure 10C:
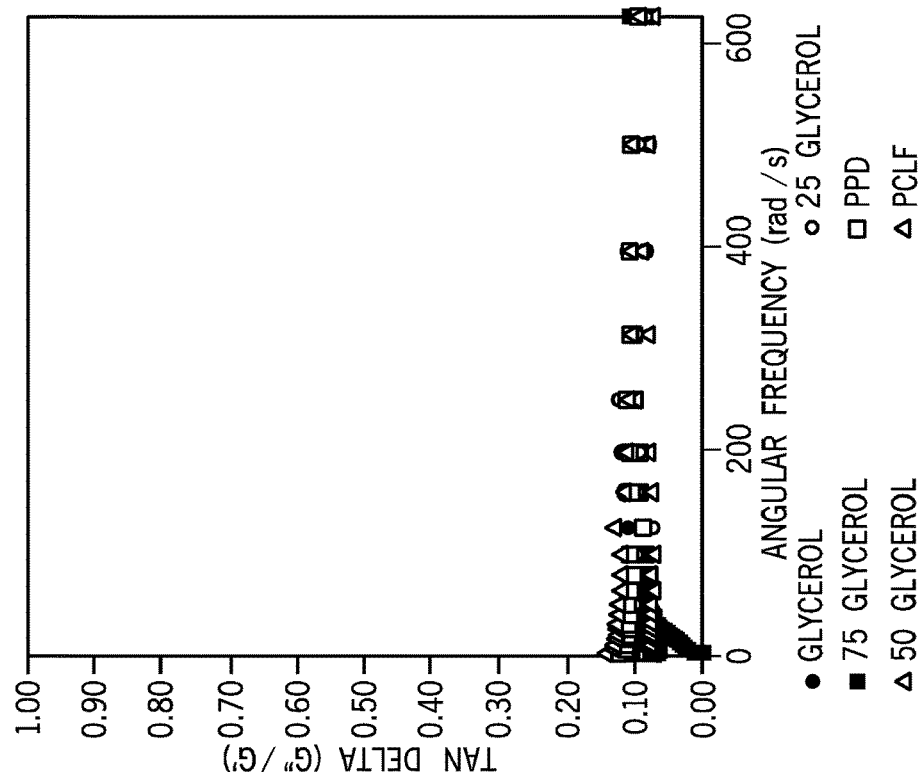
FIG. 10C shows rheological measurements for tan δ as a function of frequency for different PCLF compositions after autoclave sterilization.
Figure 11:
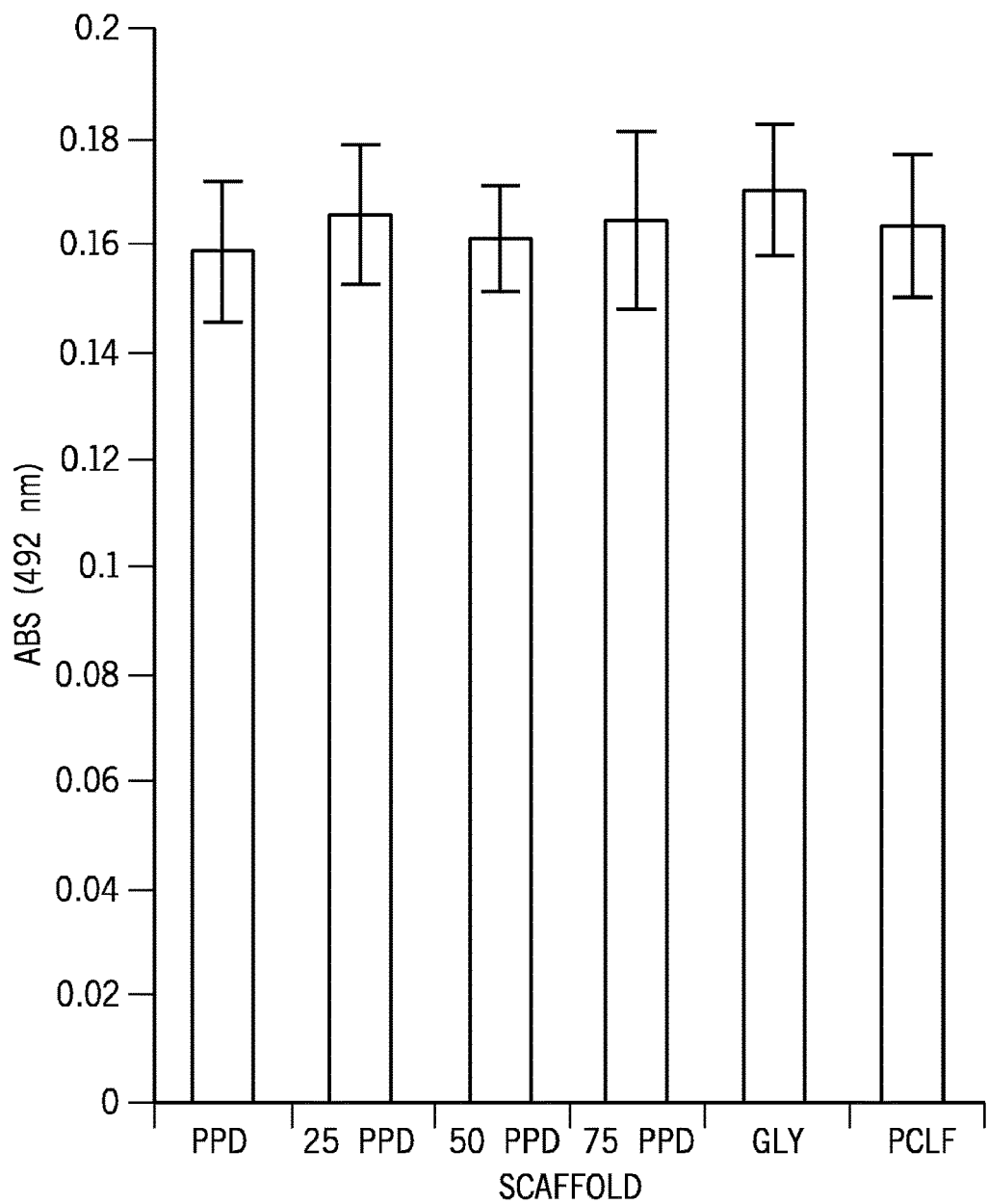
Figure 11A:
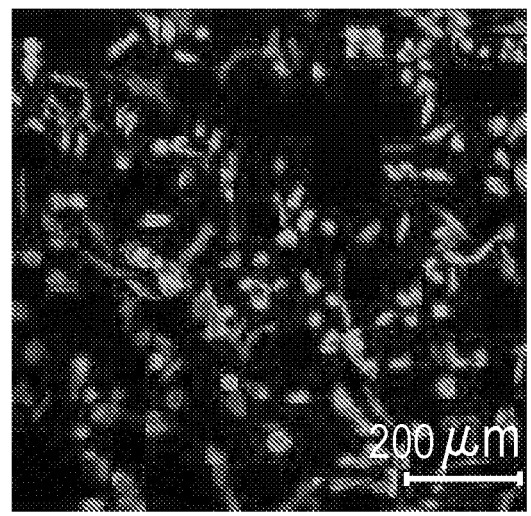
Figure 11B:
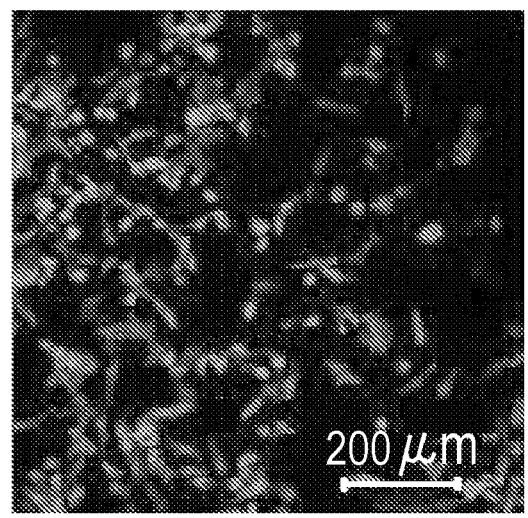
Figure 11C:
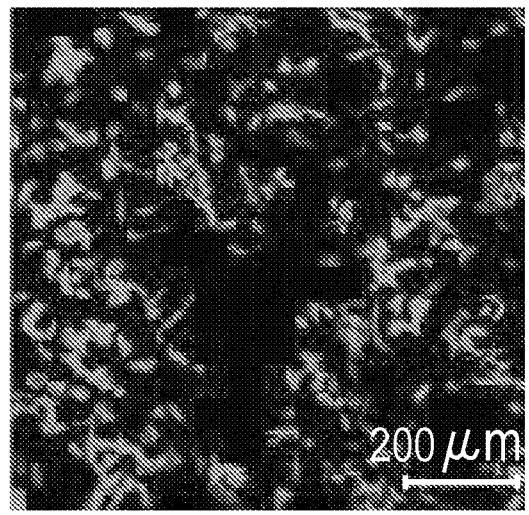
Figure 11D:
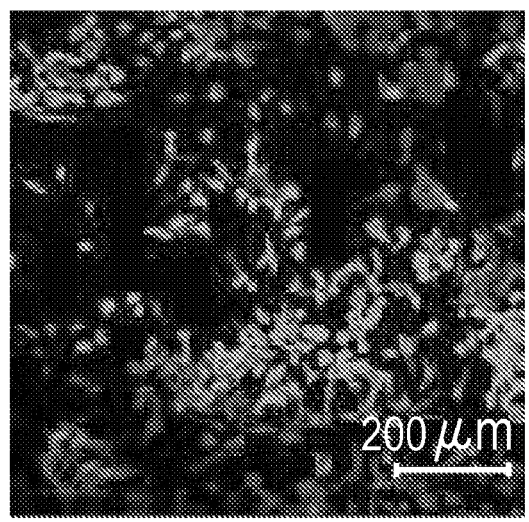
Figure 11E:
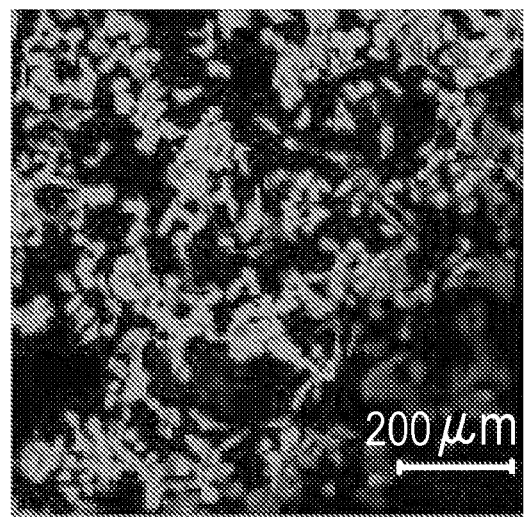
Figure 11F:
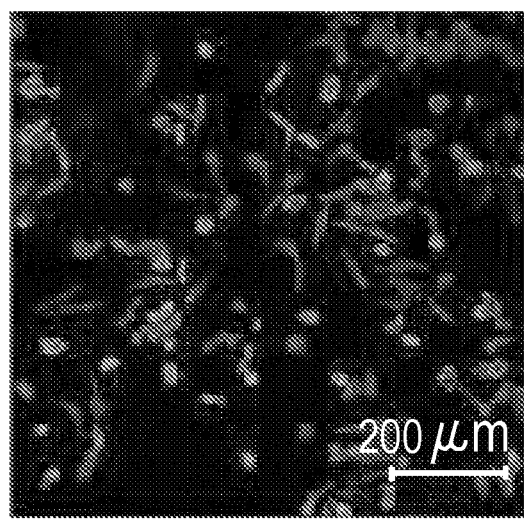

Rheological measurements were performed 1 day after sterilization and the results are shown in FIGS. 10A to 10D. Only subtle differences were observed for G', G" and tan δ for all materials when compared to the properties before sterilization. For instance, G' for PCLF$_{GLY}$ decreased from 2.6 MPa to 1.5 MPa after sterilization. This difference in G' and G" translated into increased compliance behavior when a constant shear stress was applied as shown in FIG. 10D. PCLF$_{GLY}$ exhibited an increase from 4 to 6.2%. Other PCLF materials also showed changes in the G' and G" that changed their compliance behavior, although no PCLF exhibited a material behavior dramatically different from those measured before the autoclave sterilization process.

III. Discussion

PCL$_{PPD}$ is a linear polymer architecture similar to commercially available PCL$_{DEG}$, however PCL$_{GLY}$ is tribranched star polymer. The tri-branched star polymer, because the over molecular weights are designed to be the same, the individual PCL chains are shorter for PCL$_{GLY}$ than for PCL$_{PPD}$ or PCL$_{DEG}$.

A. Characterization of Thermal Transitions and Crystalline Properties

The crystalline nature of a polymeric material dramatically affects its mechanical properties. PCLF is a semi-crystalline material that possesses a T$_m$ very close to physiological temperatures. It is important to understand how a material acts thermally because the crystalline regions are a significant contributor to a materials strength. Therefore the mechanical properties can vary dramatically depending whether PCLF is in its crystalline or amorphous state. The DSC data shows that linear $PCLF_{PPD}$ and $PCLF_{DEG}$ have similar thermal and crystalline properties as expected because the polymeric composition and architecture are identical except for the initiator that is about 5% of the total composition. $PCLF_{GLY}$ has a decreased percent crystallinity and $T_m$ compared to the linear $PCLF_{PPD}$ or $PCLF_{DEG}$. The decrease in crystallinity is attributed to the effect of branching. Polymeric branching as well as increasing cross-link density can disrupt the crystallization process by reducing the chain motion necessary for folding and ultimate crystal formation. $PCL_{GLY}$ is a tri-branched polymer, however the resulting $PCLF_{GLY}$ theoretically has multiple branching points along the backbone, which the likely reason for the decreased crystallinity. As a result of the branching the individual PCL chains are shorter (7 monomer units) than the linear counterparts (9-10 monomer units) and this could also play a role in decreased crystallinity. However, this contribution is minor as Wang et al. showed that linear PCLF with 5-6 monomer units per chain and cross-linked under the same conditions exhibited a $T_m$ of 31.6° C. and 30% crystallinity (See, Wang, S.; Yaszemski, M. J.; Gruetzmacher, J. A.; Lu, L, "Photo-Crosslinked Poly(epsilon-caprolactone fumarate) Networks: Roles of Crystallinity and Crosslinking Density in Determining Mechanical Properties", Polymer (Guildf) 2008; 49:5692-99).

By changing the PCLF architecture, the $T_m$ can be tuned to be above or below 37° C. Because of this, whether the material is in a crystalline or amorphous state near physiological temperatures is critical for material performance. To determine where these thermal transitions occur, differential scanning calorimetry (DSC) was performed and the heating and cooling traces are shown in FIG. 5.

B. Rheological Properties

Rheology was used to investigate the effect of microstructure differences on the gel cross-linked polymeric shear strength. Frequency sweeps reveal that G' and G" showed no frequency dependence for all materials except for $PCLF_{GLY}$ that exhibits slight frequency dependence behavior. This indicates that all scaffolds possess a well ordered three-dimensional structure. The differences in G' observed between PCLF materials agrees with the crystallization data and are attributed to the increasing percent crystallinity, $T_m$ and $T_c$ transitions. This means that $PCLF_{DEG}$ and $PCLF_{PPD}$ exhibit the highest G' and that G' decreases with increasing percent $PCLF_{GLY}$.

C. Autoclave Sterilization

A clinically relevant sterilization protocol is a critical point for biomaterial/medical device development that is often over looked during initial polymer development, in vitro work, and even in vivo studies where simple sterilization with 70% alcohol will suffice. Autoclave is the most commonly used sterilization technique for surgical instruments, however for easily degradable and non cross-linked polymeric materials it can destroy the scaffold geometry or detrimentally affect the material properties and the ultimate device performance. The effect of autoclave sterilization on PCLF properties was investigated because PCLF is hydrophobic, cross-linked, and more slowly degrading than other polyesters and therefore more resilient to autoclave sterilization.

IV. Conclusion

Polycaprolactone fumarate materials were successfully synthesized from biocompatible 1,2 propane diol or glycerol initiated polycaprolactone precursors to eliminate the undesirable diethylene glycol component of previous polycaprolactone fumarate compositions. The linear $PCLF_{PPD}$ polymeric scaffolds maintain thermal, rheological, and mechanical properties similar to $PCLF_{DEG}$, while the branched $PCLF_{GLY}$ can be used to tune the material properties. The branched structure of $PCLF_{GLY}$ disrupts crystallization resulting in reduced % crystallinity and $T_m$ below physiological temperatures. This makes $PCLF_{GLY}$ amorphous and changes its mechanical behavior to be elastomeric rather than purely elastic. Additionally it was shown that these polycaprolactone fumarate materials can be sterilized by autoclave with little change in the material properties.

Thus, the invention provides a biocompatible polycaprolactone fumarate formulation that releases no diethylene glycol or other undesirable byproducts during degradation.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A scaffold for tissue regeneration, the scaffold comprising:
a blend of a polymer having the Formula (I)

$$H\text{-}A_1\text{-}B\text{-}A_2\text{-}C\text{-}A_1\text{-}B\text{-}A_2\text{-}H \qquad (I)$$

wherein
$A_1$ is

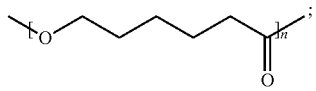

$A_2$ is

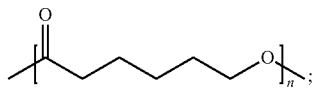

B is —O—X—O— wherein X is selected from the group consisting of ethylene, trimethylene, tetramethylene, pentamethylene, $C_1$-$C_5$alkylethylene, $C_1$-$C_5$alkyltrimethylene, $C_1$-$C_5$alkyltetramethylene, and $C_1$-$C_5$alkylpentamethylene;

C is

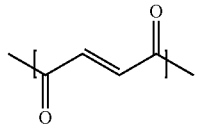

and geometric isomers thereof;
and n is an integer from 1 to 50, and
a polymer having the Formula (II)

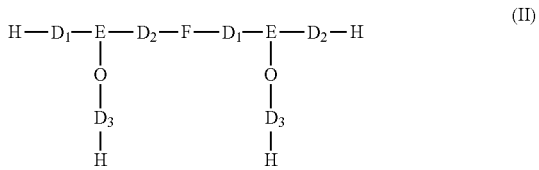

wherein
D₁ is

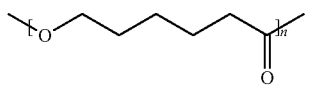

D₂ is

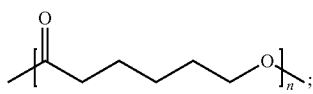

D₃ is

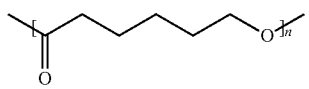

E is —O—X—O— wherein X is selected from the group consisting of propanetriyl, butanetriyl, pentanetriyl, C₁-C₅alkyl propanetriyl, C₁-C₅alkyl butanetriyl, and C₁-C₅alkyl pentanetriyl;
F is

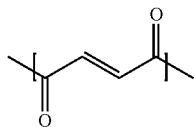

and geometric isomers thereof;
and n is an integer from 1 to 50;
wherein the polymer of Formula (I) comprises 20 wt. % to 80 wt % of the scaffold, and the polymer of Formula (II) comprises 20 wt. % to 80 wt % of the scaffold, and
wherein the polymer of Formula (I) is formed using a first initiator such that B is —O—X—O— wherein X is selected from the group consisting of ethylene, trimethylene, tetramethylene, pentamethylene, C₁-C₅alkylethylene, C₁-C₅alkyltrimethylene, C₁-C₅alkyltetramethylene, and C₁-C₅alkylpentamethylene, and
wherein the polymer of Formula (II) is formed using a second initiator such that E is —O—X—O— wherein X is selected from the group consisting of propanetriyl, butanetriyl, pentanetriyl, C₁-C₅alkyl propanetriyl, C₁-C₅alkyl butanetriyl, and C₁-C₅alkyl pentanetriyl, and
wherein the first initiator is different from the second initiator.

2. The scaffold of claim 1 wherein:
the polymer of Formula (I) comprises 40 wt. % to 60 wt % of the scaffold, and
the polymer of Formula (II) comprises 40 wt. % to 60 wt % of the scaffold.

3. The scaffold of claim 1 wherein:
in the polymer of Formula (I), X is methylethylene.

4. The scaffold of claim 1 wherein the polymer of Formula (I) has a number average molecular weight in the range of 5,000 to 15,000 g mol⁻¹.

5. The scaffold of claim 1 wherein:
in the polymer of Formula (II), X is propanetriyl.

6. The scaffold of claim 1 wherein the polymer of Formula (II) has a number average molecular weight in the range of 5,000 to 15,000 g mol⁻¹.

7. The scaffold of claim 1 wherein:
the scaffold maintains its geometrical structure and dimensions throughout an autoclave sterilization process, and
the scaffold maintains mechanical properties within an order of magnitude during the autoclave sterilization process.

8. The scaffold of claim 1 wherein:
diethylene glycol is not released during hydrolysis of the scaffold.

9. The scaffold of claim 1 wherein:
the scaffold has a fracture stress in a range of 2 to 8 MPa.

10. The scaffold of claim 1 wherein:
the scaffold has a tensile modulus in a range of 20 to 80 MPa.

* * * * *